United States Patent
Shoshan-Barmatz

(10) Patent No.: US 11,286,533 B2
(45) Date of Patent: Mar. 29, 2022

(54) BIOMARKERS OF CHRONIC LYMPHOCYTIC LEUKEMIA AND USE THEREOF

(71) Applicant: THE NATIONAL INSTITUTE FOR BIOTECHNOLOGY IN THE NEGEV LTD., Beer Sheva (IL)

(72) Inventor: Varda Shoshan-Barmatz, Omer (IL)

(73) Assignee: THE NATIONAL INSTITUTE FOR BIOTECHNOLOGY IN THE NEGEV LTD., Beer Sheva (IL)

( * ) Notice: Subject to any disclaimer, the term of this patent is extended or adjusted under 35 U.S.C. 154(b) by 659 days.

(21) Appl. No.: 16/063,784

(22) PCT Filed: Dec. 19, 2016

(86) PCT No.: PCT/IL2016/051354
§ 371 (c)(1),
(2) Date: Jun. 19, 2018

(87) PCT Pub. No.: WO2017/109774
PCT Pub. Date: Jun. 29, 2017

(65) Prior Publication Data
US 2020/0270701 A1    Aug. 27, 2020

Related U.S. Application Data

(60) Provisional application No. 62/289,951, filed on Feb. 2, 2016, provisional application No. 62/269,990, filed on Dec. 20, 2015.

(51) Int. Cl.
| | | |
|---|---|---|
| *C12Q 1/6886* | (2018.01) | |
| *G01N 33/49* | (2006.01) | |
| *A61K 48/00* | (2006.01) | |
| *C12N 15/113* | (2010.01) | |
| *A61K 45/06* | (2006.01) | |
| *C07K 16/00* | (2006.01) | |

(52) U.S. Cl.
CPC ........... *C12Q 1/6886* (2013.01); *G01N 33/49* (2013.01); *A61K 45/06* (2013.01); *A61K 48/00* (2013.01); *C07K 16/00* (2013.01); *C12N 15/1135* (2013.01); *C12Q 2600/112* (2013.01); *C12Q 2600/158* (2013.01); *G01N 2800/52* (2013.01); *G01N 2800/56* (2013.01)

(58) Field of Classification Search
CPC ............. G01N 33/49; G01N 2800/56; G01N 2800/50; A61K 48/00; A61K 45/06; C07K 16/00; C12N 15/1135; C12N 2310/14; A61P 35/00
See application file for complete search history.

(56) References Cited

U.S. PATENT DOCUMENTS

| | | | |
|---|---|---|---|
| 4,196,265 A | 4/1980 | Croce et al. | |
| 8,623,601 B2 | 1/2014 | Vitek | |

FOREIGN PATENT DOCUMENTS

| | | | | |
|---|---|---|---|---|
| WO | 1995022618 A1 | 8/1995 | | |
| WO | 2006094747 A1 | 9/2006 | | |
| WO | 2006113679 A2 | 10/2006 | | |
| WO | 2007058623 A1 | 5/2007 | | |
| WO | WO-2009033743 A1 * | 3/2009 | ............ | C07K 16/18 |
| WO | 2010011317 A1 | 1/2010 | | |
| WO | 2010019921 A2 | 2/2010 | | |
| WO | WO-2010019921 A2 * | 2/2010 | ........... | C12Q 1/6809 |
| WO | 2012104836 A1 | 8/2012 | | |
| WO | 2013010140 A2 | 1/2013 | | |
| WO | 2013035095 A1 | 3/2013 | | |

OTHER PUBLICATIONS

Affymetrix 2001. GeneChip Human Genome U133 Set. Two pages. (Year: 2001).*
Results. NetAffx Search for SNX18. Obtained on Sep. 25, 2020 from https://www.affymetrix.com/analysis/netaffx/showresults.affx. one page (Year: 2020).*
Carlucci, F., et al. A 57-gene expression signature inB-cell chronic lymphocytic leukemia. Biomedicine & pharmacotherapy, 2009, 63.9: 663-671 (Year: 2009).*
Wang et al., (2011) SF3B1 and other novel cancer genes in chronic lymphocytic leukemia. New England Journal of Medicine, 365(26), 2497-2506.
Weinberg et al., (2007) Clinical and molecular predictors of disease severity and survival in chronic lymphocytic leukemia. Am J Hematol 82(12): 1063-1070.
Admoni-Elisha et al., (2016) Novel biomarker proteins in chronic lymphocytic leukemia: impact on diagnosis, prognosis and treatment. PloS one, 11(4), e0148500.
Alsagaby et al., (2014) Proteomics-based strategies to identify proteins relevant to chronic lymphocytic leukemia. Journal of proteome research, 13(11), 5051-5062.
Ashburner et al., (2000) Gene Ontology: tool for the unification of biology. Nature genetics, 25(1), 25-29.
Binet et al., (1981) A new prognostic classification of chronic lymphocytic leukemia derived from a multivariate survival analysis. Cancer, 48(1), 198-206.
Binet et al., (2006) Perspectives on the use of new diagnostic tools in the treatment of chronic lymphocytic leukemia. Blood, 107(3), 859-861.

(Continued)

*Primary Examiner* — Gregory S Emch
(74) *Attorney, Agent, or Firm* — Browdy and Neimark, PLLC

(57) ABSTRACT

The present invention provides novel biomarkers of chronic lymphocytic leukemia (CLL). Specifically, the present invention provides methods and kits for diagnosing, assessing the level of severity, and treating of CLL.

10 Claims, 17 Drawing Sheets

Specification includes a Sequence Listing.

(56) References Cited

OTHER PUBLICATIONS

Binnet, (1989) Chronic lymphocytic leukemia: recommendations for diagnosis, staging, and response criteria. Ann Intern Med., 110, 236-238.
Byrd et al., (2006) Select high-risk genetic features predict earlier progression following chemoimmunotherapy with fludarabine and rituximab in chronic lymphocytic leukemia: justification for risk-adapted therapy. Journal of Clinical Oncology, 24(3), 437-443.
Carlucci et al., (2009) A 57-gene expression signature in B-cell chronic lymphocytic leukemia. Biomedicine & pharmacotherapy, 63(9), 663-671.
Catovsky et al., (1989) Prognostic factors in chronic lymphocytic leukaemia: the importance of age, sex and response to treatment in survival. British journal of haematology, 72(2), 141-149.
Catovsky et al., (2007) Assessment of fludarabine plus cyclophosphamide for patients with chronic lymphocytic leukaemia (the LRF CLL4 Trial): a randomised controlled trial. The Lancet, 370(9583), 230-239.
Chopra et al., (2013) Identification of novel compounds that enhance colon cancer cell sensitivity to inflammatory apoptotic ligands. Cancer biology & therapy, 14(5), 436-449.
CLL Trialists' CollaborativeGroup, (1999) Chemotherapeutic options in chronic lymphocytic leukemia: a meta-analysis of the randomized trials. Journal of the National Cancer Institute, 91(10), 861-868.
Crespo et al., (2003) ZAP-70 expression as a surrogate for immunoglobulin-variable-region mutations in chronic lymphocytic leukemia. New England Journal of Medicine, 348(18), 1764-1775.
Damle et al., (1999) Ig V Gene Mutation Status and CD38 Expression as Novel Prognostic Indicators in Chronic Lymphocytic Leukemia: Presented in part at the 40th Annual Meeting of The American Society of Hematology, held in Miami Beach, FL, Dec. 4-8, 1998. Blood, 94(6), 1840-1847.
Del Giudice et al., (2009) Spontaneous regression of chronic lymphocytic leukemia: clinical and biologic features of 9 cases. Blood, 114(3), 638-646.
Di Giovanni et al., (1989) Beta-2-microglobulin is a reliable tumor marker in chronic lymphocytic leukemia. Acta haematologica, 81(4), 181-185.
Di Pietro et al., (2006) BLOC-1 interacts with BLOC-2 and the AP-3 complex to facilitate protein trafficking on endosomes. Molecular biology of the cell, 17(9), 4027-4038.
Dighiero et al., (1998) Chlorambucil in indolent chronic lymphocytic leukemia. New England Journal of Medicine, 338(21), 1506-1514.
Döhner et al., (2000) Genomic aberrations and survival in chronic lymphocytic leukemia. New England Journal of Medicine, 343(26), 1910-1916.
Faguet, (1994) Chronic lymphocytic leukemia: an updated review. Journal of Clinical Oncology, 12(9), 1974-1990.
Gene Ontology Consortium, (2014) Gene ontology consortium: going forward. Nucleic acids research, 43(D1), D1049-D1056.
Ghia et al., (2003) The pattern of CD38 expression defines a distinct subset of chronic lymphocytic leukemia (CLL) patients at risk of disease progression. Blood, 101(4), 1262-1269.
Grever et al., (2007) Comprehensive assessment of genetic and molecular features predicting outcome in patients with chronic lymphocytic leukemia: results from the US Intergroup Phase III Trial E2997. Journal of Clinical Oncology, 25 (7), 799-804.
Hamblin et al., (1999) Unmutated Ig VH genes are associated with a more aggressive form of chronic lymphocytic leukemia. Blood, 94(6), 1848-1854.
Höög et al., (2001) Mammalian alcohol dehydrogenase—functional and structural implications. Journal of biomedical science, 8(1), 71-76.
Hoyer et al., (1995) True T-cell chronic lymphocytic leukemia: a morphologic and immunophenotypic study of 25 cases [see comments]. Blood, 86(3), 1163-1169.
Huang et al., (2008) Systematic and integrative analysis of large gene lists using DAVID bioinformatics resources. Nature protocols, 4(1), 44-57.
Kanehisa & Goto, (2000) KEGG: kyoto encyclopedia of genes and genomes. Nucleic acids research, 28(1), 27-30.
Kanehisa et al., (2013) Data, information, knowledge and principle: back to metabolism in KEGG. Nucleic acids research, 42(D1), D199-D205.
Kelstrup et al., (2012) Optimized fast and sensitive acquisition methods for shotgun proteomics on a quadrupole orbitrap mass spectrometer. Journal of proteome research, 11(6), 3487-3497.
Khanna et al., (2001) Metastasis-associated differences in gene expression in a murine model of osteosarcoma. Cancer research, 61(9), 3750-3759.
Kröber et al., (2002) V H mutation status, CD38 expression level, genomic aberrations, and survival in chronic lymphocytic leukemia. Blood, 100(4), 1410-1416.
Kröber et al., (2006) Additional genetic high-risk features such as 11q deletion, 17p deletion, and V3-21 usage characterize discordance of ZAP-70 and VH mutation status in chronic lymphocytic leukemia. Journal of Clinical Oncology, 24(6), 969-975.
Kruger & von Schaewen, (2003) The oxidative pentose phosphate pathway: structure and organisation. Current opinion in plant biology, 6(3), 236-246.
Li et al., (2015) Lentiviral DDX46 knockdown inhibits growth and induces apoptosis in human colorectal cancer cells. Gene, 560(2), 237-244.
Linder & Jankowsky, (2011) From unwinding to clamping—the DEAD box RNA helicase family. Nature reviews Molecular cell biology, 12(8), 505.
Maddocks-Christianson et al., (2007) Risk factors for development of a second lymphoid malignancy in patients with chronic lymphocytic leukaemia. British journal of haematology, 139(3), 398-404.
Melle et al., (2006) Identification of specific protein markers in microdissected hepatocellular carcinoma. Journal of proteome research, 6(1), 306-315.
Miretti et al., (2008) A mouse model of pulmonary metastasis from spontaneous osteosarcoma monitored in vivo by Luciferase imaging. PloS one, 3(3), e1828, 1-8.
Montserrat et al., (1986) Lymphocyte doubling time in chronic lymphocytic leukaemia: analysis of its prognostic significance. British journal of haematology, 62(3), 567-575.
Orchard et al., (2004) ZAP-70 expression and prognosis in chronic lymphocytic leukaemia. The Lancet, 363(9403), 105-111.
Rai et al., (1975) Clinical staging of chronic lymphocytic leukemia. Blood, 46(2), 219-234.
Rassenti et al., (2004) ZAP-70 compared with immunoglobulin heavy-chain gene mutation status as a predictor of disease progression in chronic lymphocytic leukemia. New England Journal of Medicine, 351(9), 893-901.
Rosenwald et al., (2001) Relation of gene expression phenotype to immunoglobulin mutation genotype in B cell chronic lymphocytic leukemia. Journal of Experimental Medicine, 194(11), 1639-1648.
Rossi & Gaidano, (2012) Molecular genetics of high-risk chronic lymphocytic leukemia. Expert review of hematology, 5(6), 593-602.
Selcuklu et al., (2012) MicroRNA-9 inhibition of cell proliferation and identification of novel miR-9 targets by transcriptome profiling in breast cancer cells. Journal of Biological Chemistry, 287(35), 29516-29528.
Shanafelt et al., (2006) Prospective evaluation of clonal evolution during long-term follow-up of patients with untreated early-stage chronic lymphocytic leukemia. Journal of Clinical Oncology, 24(28), 4634-4641.
Stacchini et al., (1999) MEC1 and MEC2: two new cell lines derived from B-chronic lymphocytic leukaemia in prolymphocytoid transformation. Leukemia research, 23(2), 127-136.
Takafumi et al., (2001) Structure and expression of human mitochondrial adenylate kinase targeted to the mitochondrial matrix. Biochemical journal, 358(1), 225-232.
Ueda et al., (2011) A comprehensive peptidome profiling technology for the identification of early detection biomarkers for lung adenocarcinoma. PLoS One, 6(4), e18567, 1-12.

\* cited by examiner

BIOMARKERS OF CHRONIC LYMPHOCYTIC LEUKEMIA AND USE THEREOF

FIELD OF THE INVENTION

The present invention relates to biomarkers of chronic lymphocytic leukemia. In particular, the present invention relates to means and methods for diagnosing, assessing the level of severity and treating of chronic lymphocytic leukemia.

BACKGROUND OF THE INVENTION

Chronic lymphocytic leukemia (CLL), a B cell non-Hodgkin's lymphoma with a leukemic appearance, is the most common leukemia of adults in Western countries, with median age at diagnosis ranging between 67 and 72 years. Recent data indicate that approximately 6% of the normal elderly population develops a monoclonal B-cell lymphocytosis (MBL), which can transform into CLL in 1%-2% of cases. The clinical course is highly variable, ranging from very indolent cases to patients with aggressive and rapidly progressing disease. This heterogeneity has important consequences which impacts clinical approaches, treatment strategies, and survival time from diagnosis.

CLL patients are currently categorized into risk groups based on the clinical staging systems developed by Rai et al. (*Blood.* 1975; 46(2):219-234) and Binet et al. in the early 1980s (*Cancer.* 1981; 48(1):198-206). These classifications are still helpful for dividing patients in regard to the expected overall survival (OS). However, both systems fail to indicate higher risk of progression among patients in early stages of the disease. Later, additional prognostic markers based on peripheral blood or bone marrow examination, such as an identification of atypical morphology of CLL cells, high rate of prolymphocytes, or diffuse infiltration of bone marrow, which are associated with worse outcome, were reported. Among newer prognostic factors in CLL, there are lymphocyte doubling time (LDT), serum markers, biological prognostic factors (IGHV) mutational status, ZAP-70 expression, CD38 expression, and cytogenetic abnormalities.

In spite of considerable research into therapies for CLL, a need remains to diagnose and treat CLL effectively, and the mortality observed in patients indicates that improvements are needed in the diagnosis, treatment and prevention of the disease. Treatment should be introduced in patients with advanced, symptomatic, or progressive disease. Chemotherapy and immunotherapy are usually used to treat CLL. The choice of therapy depends on clinical stage, the disease activity, age, and existing comorbidities.

U.S. Pat. No. 8,623,601 discloses a method of predicting or assessing the level of severity of cancer or cancer progression in a patient diagnosed with chronic lymphocytic leukemia or B-cell non-Hodgkin's lymphoma comprising determining the ratio of SET alpha isoform to SET beta isoform in B lymphocytes isolated from the patient and comparing the ratio of SET alpha isoform to SET beta isoform to the ratio in a control sample or a standard value, wherein an increase in the ratio of SET alpha isoform to SET beta isoform relative to the ratio in the control sample or standard value is indicative of a more severe form of cancer or later stage of cancer progression in the patient.

International Application Publication No. WO 2013/035095 to the inventor of the present invention discloses methods and kits for the detection of cancer and for pre-cancer screening based on the expression of genes associated with altered metabolism and apoptosis in cancerous cells, particularly the expression of a mitochondrial antiviral-signaling (MAVS) and/or a voltage-dependent anion channel 1 (VDAC1) protein or mRNA in combination with additional genes associated with cell metabolism and/or apoptosis.

There remains an unmet need for adequate biomarkers that are suitable as diagnostic tools for assessing the presence or absence of chronic lymphocytic leukemia, assessing CLL severity, and being a target for anticancer therapy.

SUMMARY OF THE INVENTION

The present invention relates to novel biomarkers which are differentially expressed in chronic lymphocytic leukemia (CLL) patients and/or according to the severity of the disease. The present invention in some embodiments provides methods of diagnosing chronic lymphocytic leukemia (CLL). The present invention further provides in additional embodiments methods of prognosis of patients diagnosed to have chronic lymphocytic leukemia (CLL). In addition, the present invention provides methods of treating chronic lymphocytic leukemia according to the diagnosis and/or prognosis.

The present invention is based in part on the unexpected discovery that the expression levels of specific proteins present in a biological sample obtained from a human subject can be used as diagnostic and/or prognostic indicators of cancer, particularly CLL, cancer severity, or cancer progression.

The expression level of the proteins DDX46, AK3, AP3B1, ADH5, BRI3B, IDH3A, SNX18, RPE and PPWD1, individually or in combinations, was found to be increased, and the level of LTBP1 was found to be decreased in peripheral blood mononuclear cells (PBMCs) obtained from patients diagnosed with CLL disease or having a severe appearance of the disease. In addition, an increase in the expression of SNX18, DHRS4, TBL2, and RPE proteins and decrease in the expression of ENPP4 were found to be associated with a likelihood of significant deterioration of the disease in CLL-diagnosed patients. A combination of proteins that have a wide variety of cellular activities according to the teachings of the present invention ensures a precise and adequate diagnostic tool.

According to one aspect, the present invention provides a method for diagnosing chronic lymphocytic leukemia (CLL) in a subject, the method comprising:
 (i) comparing the expression level of at least one protein or mRNA biomarker in a biological sample of the subject to a reference value or a control sample, wherein said at least one biomarker is selected from the group consisting of DDX46, AK3, AP3B1, ADH5, BRI3B, IDH3A, SNX18, RPE, PPWD1, LTBP1, and any combination thereof;
 (ii) diagnosing the subject as having CLL wherein the expression level of the at least one biomarker selected from DDX46, AK3, AP3B1, ADH5, BRI3B, IDH3A, SNX18, RPE and PPWD1 is increased, or wherein the expression level of LTBP1 is decreased in the sample as compared to the reference value or control sample.

According to some embodiments, step (i) comprises comparing the expression level of at least two protein or mRNA biomarkers selected from the group consisting of: DDX46, AK3, AP3B1, ADH5, BRI3B, IDH3A, SNX18, RPE, LTBP1, and PPWD1. Each possibility represents a separate embodiment of the present invention. According to other embodiments, step (i) comprises comparing the expression level of at least three protein or mRNA biomarkers selected from the group consisting of: DDX46, AK3, AP3B1, ADH5, BRI3B, IDH3A, SNX18, RPE and LTBP1, and PPWD1. Each possibility represents a separate embodiment of the present invention. According to other embodiments, step (i) comprises comparing the expression level of at least four protein or mRNA biomarkers selected from the group consisting of: DDX46, AK3, AP3B1, ADH5, BRI3B, IDH3A, SNX18, RPE, LTBP1, and PPWD1. Each possibility represents a separate embodiment of the present invention. According to other embodiments, step (i) comprises comparing the expression level of at least five protein or mRNA biomarkers selected from the group consisting of: DDX46, AK3, AP3B1, ADH5, BRI3B, IDH3A, SNX18, RPE, LTBP1, and PPWD1. Each possibility represents a separate embodiment of the present invention. According to certain embodiments, step (i) comprises comparing the expression level of at least six protein or mRNA biomarkers selected from the group consisting of: DDX46, AK3, AP3B1, ADH5, BRI3B, IDH3A, SNX18, RPE, LTBP1, and PPWD1 biomarkers. Each possibility represents a separate embodiment of the present invention. According to certain embodiments, step (i) comprises comparing the expression level of DDX46, AK3, AP3B1, ADH5, BRI3B, IDH3A, SNX18, RPE, LTBP1, and PPWD1 protein or mRNA biomarkers.

According to some embodiments, step (i) comprises comparing the expression level of AK3 and DDX46 biomarkers. According to additional embodiments, step (i) comprises comparing the expression level of PPWD1 biomarker. According to additional embodiments, step (i) comprises comparing the expression level of DDX46, AK3, AP3B1, and ADH5.

According to specific embodiments, step (i) comprises comparing the expression level of the DDX46, AK3, AP3B1, ADH5, BRI3B, IDH3A, SNX18, RPE, LTBP1 and PPWD1 biomarkers.

According to some embodiments, the reference value or the control sample is obtained from healthy subject.

According to some embodiments, the reference value is an average value determined in a plurality of samples obtained from healthy subjects.

According to some embodiments, the method further comprises determining the level of one or more additional biomarkers, wherein the additional biomarker is selected from the group consisting of: VDAC1, MAVS, SMAC, AIF, BCl-2, GELS, HK-1 and combinations thereof. Each possibility represents a separate embodiment of the present invention.

According to some embodiments, the biomarker is selected from the group consisting of a protein and a polynucleotide. According to certain embodiments, the at least one biomarker is a protein and the expression level is detected using mass spectrometry. According to other embodiments, the at least one biomarker is a protein and the expression level is measured using an antibody specifically interacting with said at least one biomarker. According to other embodiments, the biomarkers comprise a plurality of proteins and the expression level is measured using an antibody microarray comprising antibodies specific for the plurality of biomarkers of the present invention.

According to some embodiments, the biomarker is mRNA. According to certain embodiments, the biomarker is mRNA and the expression level is detected by employing a Nucleic acid testing (NAT)-based technology. In one embodiment, the NAT-based assay is selected from the group consisting of a PCR, Real-Time PCR, LCR, Self-Sustained Synthetic Reaction, Q-Beta Replicase, Cycling Probe Reaction, Branched DNA, RFLP analysis, DGGE/TGGE, Single-Strand Conformation Polymorphism, Dideoxy Fingerprinting, Microarrays, Fluorescence, In Situ Hybridization or Comparative Genomic Hybridization, and high-throughput transcriptome analysis. According to certain embodiments, the high-throughput transcriptome analysis comprises high-throughput sequencing technologies.

According to some embodiments, the expression level is increased by at least 2-fold relative to the reference values and/or control sample.

According to some embodiments, the method further comprises treating the subject diagnosed as having chronic lymphocytic leukemia with a therapy for chronic lymphocytic leukemia.

According to an additional aspect, the present invention provides a method of diagnosing and treating chronic lymphocytic leukemia in a subject, the method comprising:
  (i) comparing the expression level of at least one protein or mRNA biomarker in a biological sample obtained from the subject to a reference value or a control sample, wherein said at least one biomarker is selected from the group consisting of: DDX46, AK3, AP3B1, ADH5, BRI3B, IDH3A, SNX18, RPE, LTBP1, PPWD1 and any combination thereof;
  (ii) diagnosing said subject as having CLL wherein the expression level of at least one biomarker in the sample selected from DDX46, AK3, AP3B1, ADH5, BRI3B, IDH3A, SNX18, PPWD1 and RPE is increased, or wherein the expression level of LTBP1 is decreased in the sample as compared to the reference value or control sample; and
  (iii) treating said subject diagnosed as having chronic lymphocytic leukemia with a therapy for chronic lymphocytic leukemia.

According to some embodiments, the method comprises comparing the expression level of DDX46 and AK3 biomarkers.

According to some embodiments, step (i) comprises comparing at least one protein or mRNA biomarker selected from the group consisting of DDX46, AK3, AP3B1, and ADH5.

It is to be explicitly understood that the level of the protein or mRNA biomarkers at additional biomarker combinations as can be determined by the skilled Artisan and as described herein above can be also used with the method of diagnosing and treating chronic lymphocytic leukemia in a subject.

According to some embodiments, the method further comprises a step of evaluating the severity of the CLL in a subject diagnosed with CLL and treating said subject according to the severity. Evaluating the severity of the CLL can be performed as is known in the art and as described herein.

According to some embodiments, step (iii) comprises treating the subject diagnosed with CLL with a treatment selected from the group consisting of chemotherapy, monoclonal antibodies, CLL targeted therapy and stem cell transplant. Each possibility represents a separate embodiment of the invention. According to some embodiments, the CLL targeted therapy is a siRNA, small molecule or a peptide agent targeting one of the overexpressed proteins. According to certain embodiments, the chemotherapy is selected from the group consisting of: steroids, alkylating agents, purine analogs, and combination chemotherapy. Each possibility represents a separate embodiment of the invention.

According to other embodiments, step (iii) comprises treating the subject diagnosed with CLL with an agent selected from the group consisting of Fludarabine, Cyclophosphamide, Rituximab, Chlorambucil, Bendamustine, Obinutuzumab, PCI 32765 (Ibrutinib), Idelalisib, and any combination thereof. According to certain embodiments, step (iii) comprises treating the subject diagnosed with CLL with Fludarabine, Cyclophosphamide, and Rituximab.

According to another aspect, the present invention provides a method of predicting or assessing the level of severity of cancer in a patient diagnosed with chronic lymphocytic leukemia, the method comprising:
(i) comparing the expression level of at least one protein or mRNA biomarker in a biological sample obtained from the patient to a reference value or a control sample, wherein the at least one biomarker is selected from the group consisting of: SNX18, DHRS4, TBL2, RPE, ENPP4 and any combination thereof;
(ii) determining the level of severity of cancer, wherein an increase in the level of at least one biomarker selected from the group consisting of: SNX18, DHRS4, TBL2, RPE and any combination thereof and/or a decrease in the level of ENPP4 characterizes said patient as having a severe form of chronic lymphocytic leukemia.

According to some embodiments, the severe form of CLL is characterized in a need of a treatment for said CLL cancer.

According to some embodiments, the reference value or control sample is obtained from a sample of healthy subject or a subject having a stable state of chronic lymphocytic leukemia.

According to some embodiments, the reference value is an average value determined in a plurality of samples obtained from healthy subjects or from subjects having a stable state of chronic lymphocytic leukemia.

According to some embodiments, the method comprises comparing the expression level of at least two biomarkers. According to certain embodiments, the method comprises comparing the expression level of at least three biomarkers. According to certain embodiments, the method comprises comparing the expression level of at least four biomarkers. According to certain embodiments, the method comprises comparing the expression level of five biomarkers.

According to some embodiments, the method comprises comparing the expression level of SNX18 and RPE biomarkers. According to some embodiments, the method comprises comparing the expression level of SNX18, DHRS4, TBL2, and RPE. According to some embodiments, the control sample is obtained from a healthy subject.

According to some embodiments, the biological sample is a biological fluid sample. According to some embodiments, the biological sample is whole blood or a fraction thereof. According to certain embodiments, the whole blood fraction is serum or plasma. According to additional embodiments, the biological sample is a peripheral blood mononuclear cells (PBMCs) sample.

According to some embodiments, the increase of expression level is by a ratio of at least 2-fold relative to the control sample or reference value. According to additional embodiments, the increase of expression level is by a ratio of at least 3-fold relative to the control sample or reference value.

According to some embodiments, the method further comprises treating the patient characterized as having a severe form of chronic lymphocytic leukemia with a therapy for severe chronic lymphocytic leukemia.

According to some embodiments, the patient is treated with a therapy selected from the group consisting of chemotherapy, monoclonal antibodies, CLL targeted therapy, and stem cell transplant. Each possibility represents a separate embodiment of the invention. According to some embodiments, the CLL target therapy is an siRNA, a small molecule or a peptide agent targeting one of the overexpressed proteins. According to certain embodiments, the chemotherapy is selected from the group consisting of: steroids, alkylating agents, purine analogs, and combination chemotherapy. Each possibility represents a separate embodiment of the invention. According to other embodiments, the patient is treated with an agent selected from the group consisting of Fludarabine, Cyclophosphamide, Rituximab, Chlorambucil, Bendamustine, Obinutuzumab, PCI 32765 (Ibrutinib), Idelalisib, and any combination thereof. Each possibility represents a separate embodiment of the invention. According to certain embodiments, the method comprises a step of treating the subject diagnosed with CLL with Fludarabine, Cyclophosphamide, and Rituximab.

According to certain embodiments of the present invention, comparing the expression level of at least one protein biomarker in a biological sample of the subject to a reference value comprises determining the expression level of the at least one protein or mRNA biomarker in the sample and comparing said expression level to the reference value. According to additional embodiments, comparing the expression level of at least one protein or mRNA biomarker in a biological sample of the subject to a control sample comprises determining the expression level of the at least one protein or mRNA biomarker in the sample obtained from said subject and in the control sample and comparing said determined levels.

Any method as is known in the art to identify a protein within a biological sample and determine its expression level can be used according to the teachings of the present invention. According to certain exemplary embodiments, the expression level is determined using antibodies specifically recognizing each of the proteins of the present invention and employing quantitative methods for determining its expression level.

According to another aspect, the present invention provides a method of treating chronic lymphocytic leukemia, the method comprising administering to a subject in need thereof a therapeutically effective amount of at least one agent that reduces the expression or activity of at least one protein selected from the group consisting of DDX46, AK3, AP3B1, ADH5, BRI3B, IDH3A, SNX18, RPE, and PPWD1. Each possibility represents a separate embodiment of the invention According to an additional aspect, the present invention provides a method of treating chronic lymphocytic leukemia, the method comprising administering to a subject in need thereof a therapeutically effective amount of at least one agent that reduces the expression or activity of DDX46.

According to an additional aspect, the present invention provides a method of treating chronic lymphocytic leukemia, the method comprising administering to a subject in need thereof a therapeutically effective amount of at least one agent that reduces the expression or activity of AK3.

According to an additional aspect, the present invention provides a method of treating chronic lymphocytic leukemia, the method comprising administering to a subject in need thereof a therapeutically effective amount of at least one agent that reduces the expression or activity of AP3B1.

According to an additional aspect, the present invention provides a method of treating chronic lymphocytic leukemia, the method comprising administering to a subject in need thereof a therapeutically effective amount of at least one agent that reduces the expression or activity of ADH5.

According to an additional aspect, the present invention provides a method of treating chronic lymphocytic leukemia, the method comprising administering to a subject in need thereof a therapeutically effective amount of at least one agent that reduces the expression or activity of BRI3B.

According to an additional aspect, the present invention provides a method of treating chronic lymphocytic leukemia, the method comprising administering to a subject in need thereof a therapeutically effective amount of at least one agent that reduces the expression or activity of IDH3A.

According to an additional aspect, the present invention provides a method of treating chronic lymphocytic leukemia, the method comprising administering to a subject in need thereof a therapeutically effective amount of at least one agent that reduces the expression or activity of SNX18.

According to an additional aspect, the present invention provides a method of treating chronic lymphocytic leukemia, the method comprising administering to a subject in need thereof a therapeutically effective amount of at least one agent that reduces the expression or activity of RPE.

According to an additional aspect, the present invention provides a method of treating chronic lymphocytic leukemia, the method comprising administering to a subject in need thereof a therapeutically effective amount of at least one agent that reduces the expression or activity of PPWD1.

According to some embodiments, the agent is selected from the group consisting of: a chemical agent or moiety, a protein, a peptide, and a polynucleotide molecule. According to certain embodiments, the protein is an antibody. According to other embodiments, the agent is an interfering RNA molecule. According to certain embodiments, the interfering RNA molecule is selected from the group consisting of: a shRNA, a siRNA, and a miRNA. Each possibility represents a separate embodiment of the invention.

According to certain embodiments, treating chronic lymphocytic leukemia comprises an additional treatment selected from the group consisting of chemotherapy, monoclonal antibodies, CLL targeted therapy, and stem cell transplant. Each possibility represents a separate embodiment of the invention.

According to another aspect, the present invention provides a kit for diagnosing chronic lymphocytic leukemia, comprising:
(i) at least one agent capable of detecting the expression level of at least one protein or mRNA biomarker selected from the group consisting of DDX46, AK3, AP3B1, ADH5, BRI3B, IDH3A, SNX18, RPE, LTBP1, and PPWD1 in a biological sample; and
(ii) means for comparing the expression level of the at least one biomarker in a sample obtained from a subject suspected to have CLL to the expression level of said at least one biomarker in a sample obtained from a healthy subject; or
(iii) means for comparing the expression level of the at least one biomarker in a sample obtained from a subject suspected to have CLL to a reference value.

According to some embodiments, the kit comprises means for detecting at least two biomarkers selected from the group consisting of DDX46, AK3, AP3B1, ADH5, BRI3B, IDH3A, SNX18, RPE, LTBP1, and PPWD1. According to some embodiments, the kit comprises means for detecting at least one biomarker selected from the group consisting of DDX46, AK3, AP3B1, and ADH5. According to certain embodiments, the kit comprises means for detecting the DDX46, AK3, AP3B1, ADH5 biomarkers.

According to some embodiments, the means for detecting is an antibody array comprising specific antibodies for the biomarkers of the present invention. According to other embodiments, the kit further comprises at least one reagent for performing an ELISA, an RIA, a slot blot, an immunohistochemical assay, FACS, in vivo imaging, a radio-imaging assay, or a Western blot. According to additional embodiments, the means for detecting is an ELISA plate pre-coated with specific antibodies for the biomarkers of the present invention.

According to some embodiments, the kit further comprising instruction material directing the correlation between the compared expression levels of said at least one biomarker and having CLL.

According to another aspect, the present invention provides a kit for the prognosis of chronic lymphocytic leukemia state, comprising:
(i) at least one agent capable of detecting the expression level of at least one protein or mRNA biomarker selected from the group consisting of SNX18, DHRS4, TBL2, RPE and ENPP4 in a biological sample;
(ii) means for comparing the expression level of the at least one biomarker in a sample obtained from a subject suspected to have CLL to a reference value; and
(iii) instruction material directing the correlation between the ratio of the at least one biomarker expression level to the reference level and the severity of the CLL.

According to some embodiments, the kit comprises agents capable of detecting the expression level of SNX18, DHRS4, TBL2, RPE and ENPP4 biomarkers.

Other objects, features and advantages of the present invention will become clear from the following description, examples and drawings.

DETAILED DESCRIPTION OF THE INVENTION

Figure 1:
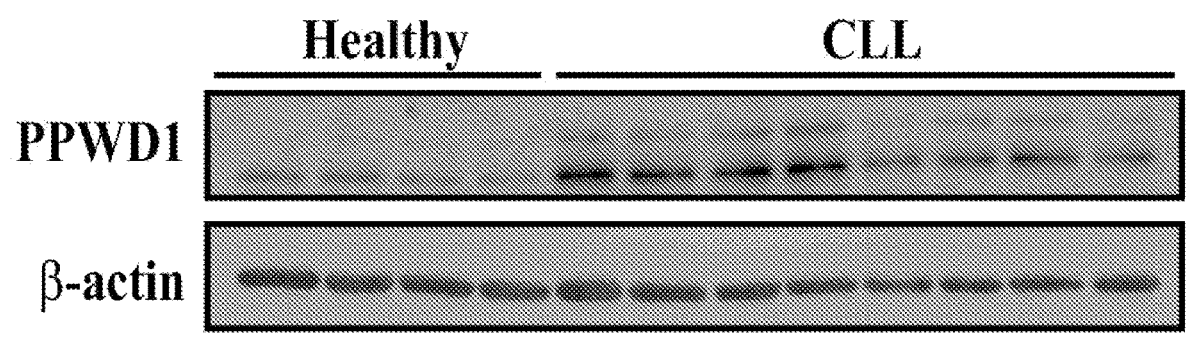
FIG. 1 shows a representative immunoblot that shows the expression levels of PPWD1 in PBMCs from healthy or CLL patients as indicated. Actin was used as loading control.

The present invention provides methods of diagnosis and prognosis of chronic lymphocytic leukemia (CLL) in a subject based on differential expression of proteins in cancer cells (PBMCS) compared to healthy cells (PBMCS). The diagnosis or prognosis can be assessed by measuring one or more of the biomarkers described herein. The present invention further provides methods of treating chronic lymphocytic leukemia by reducing the expression or activity of proteins which were found to be overexpressed in cancer cells. An early identification of a CLL patient as being expected to develop a severe form of the disease enables the selection and initiation of various therapeutic interventions or treatment regimens in order to delay, reduce, or prevent the worsening of the subject's disease.

The present invention is based on the discovery that the level of specific proteins correlates with having chronic lymphocytic leukemia and/or with the severity of the disease.

The normal control level is the level of one or more biomarkers or combined biomarker indices typically found in a subject not suffering from chronic lymphocytic leukemia. The normal and abnormal levels and cut-off points may vary based on whether a biomarker is used alone or in a formula combining with other biomarkers into an index. Alternatively, the normal or abnormal level can be a database of biomarker patterns or "signatures" from previously tested subjects who did or did not develop severe CLL. According to certain embodiments, the control level is the level of one or more biomarkers or combined marker indices found in a subject at earlier stages of CLL. According to other embodiments, the expression level of at least one biomarker is compared with the expression level in same subject prior to diagnosis.

One or more clinical parameters may be used in combination with the biomarkers of the present invention as an input to a formula or as pre-selection criteria defining a relevant population to be measured using a particular biomarker panel and formula. Clinical parameters may also be useful in the biomarker normalization and pre-processing, or in biomarker selection, formula type selection and derivation, and formula result post-processing.

According to one aspect, the present invention provides a method for diagnosing chronic lymphocytic leukemia (CLL) in a subject, the method comprising:
- (i) comparing the expression level of at least one protein or mRNA biomarker in a biological sample of the subject to a reference value or a control sample, wherein said at least one biomarker is selected from the group consisting of: DDX46, AK3, AP3B1, ADH5, BRI3B, IDH3A, SNX18, RPE, LTBP1, PPWD1, and any combination thereof;
- (ii) diagnosing the subject as having CLL wherein the expression level of the at least one biomarker selected from DDX46, AK3, AP3B1, ADH5, BRI3B, IDH3A, SNX18, PPWD1 and RPE is increased or wherein the expression level of LTBP1 is decreased in the sample as compared to the reference value or control sample.

According to some embodiments, step (i) comprises at least one biomarker selected from the group consisting of: DDX46, AK3, AP3B1, ADH5, and any combination thereof. According to certain embodiments, step (i) comprises at least two, at least three at least four, at least five, at least six, at least seven, at least eight, or at least nine biomarkers selected from the group consisting of DDX46, AK3, AP3B1, ADH5, BRI3B, IDH3A, SNX18, RPE, LTBP1, PPWD1, and any combination thereof.

According to another aspect, the present invention provides a method of predicting or assessing the level of severity of cancer in a patient diagnosed with chronic lymphocytic leukemia, the method comprising:
- (i) comparing the expression level of at least one protein or mRNA biomarker in a biological sample obtained from the patient to a reference value or a control sample, wherein the at least one biomarker is selected from the group consisting of: SNX18, DHRS4, TBL2, RPE, ENPP4, NOP56, PSMC5, CTSS, APRT, PPP2R1A, CABIN1, HP1BP3, GCD, SLC25A1, RPL13A, UBE3A, MRPS22, IGS20 and any combination thereof;
- (ii) determining the level of severity of cancer, wherein an increase in the level of at least one biomarker selected from the group consisting of: SNX18, DHRS4, TBL2, RPE, NOP56, PSMC5, CTSS, APRT, PPP2R1A, CABIN1, HP1BP3, GCD, SLC25A1, RPL13A, UBE3A, MRPS22, IGS20 and any combination thereof and/or a decrease in the level of ENPP4 characterizes said patient as having a severe form of chronic lymphocytic leukemia.

A method for diagnosing chronic lymphocytic leukemia (CLL) in a subject, the method comprising:
- (i) comparing the expression level of at least one protein or mRNA biomarker in a biological sample obtained from the subject to a reference value or a control sample, wherein said at least one biomarker is selected from the group consisting of: DDX46, AK3, AP3B1, ADH5, BRI3B, IDH3A, SNX18, RPE, PPWD1, LTBP1 and any combination thereof;
- (ii) diagnosing the subject as having CLL wherein the expression level of the at least one biomarker is altered compared to the reference value or control sample, wherein the expression level of DDX46, AK3, AP3B1, ADH5, BRI3B, IDH3A, SNX18, PPWD1 and RPE is increased, and the expression level of LTBP1 is decreased as compared to said reference value or control sample.

Definitions

The term "biomarker" as used herein refers to a protein or gene that is differentially expressed in a sample taken from a subject having CLL or severe form of CLL as compared to a comparable sample taken from a healthy subject or a CLL patient having a stable state of the disease, respectively.

The term "diagnosing" as used herein means assessing whether a subject suffers from chronic lymphocytic leukemia, or not. As will be understood by those skilled in the art, such an assessment is usually not intended to be correct for all (i.e. 100%) of the subjects to be identified. The term, however, requires that a statistically significant portion of subjects can be identified. The term diagnosis also refers, in some embodiments, to screening. Screening for cancer, in some embodiments, can lead to earlier diagnosis in specific cases.

The term "prognosis" as used herein refers to a prediction of the probable course and outcome of a clinical condition or disease. In some embodiments, the prognosis is used to differentiate between a stable state and a disease state that is expected to be exacerbated.

The term "stable state of CLL" as used herein refers to a CLL patient in a stable disease state, in which the disease condition will not worsen. According to some embodiments, the disease condition is not worsening during a period of time selected from the group consisting of at least 6 months, at least a year, at least two years, and at least three years. Each possibility represents a separate embodiment of the invention.

According to some embodiments, the method of predicting or assessing the level of severity of cancer further comprises determining the specific stage of severity according to Rai or Binet staging. According to these embodiments, the method comprises determining of the likelihood that the CLL stage of a patient will worsen.

The Rai staging system divides CLL into 5 stages:

Rai stage 0: Lymphocytosis and no enlargement of the lymph nodes, spleen, or liver, and with near normal red blood cell and platelet counts.

Rai stage I: Lymphocytosis plus enlarged lymph nodes. The spleen and liver are not enlarged and the red blood cell and platelet counts are near normal.

Rai stage II: Lymphocytosis plus an enlarged spleen (and possibly an enlarged liver), with or without enlarged lymph nodes. The red blood cell and platelet counts are near normal.

Rai stage III: Lymphocytosis plus anemia (too few red blood cells), with or without enlarged lymph nodes, spleen, or liver. Platelet counts are near normal.

Rai stage IV: Lymphocytosis plus thrombocytopenia (too few blood platelets), with or without anemia, enlarged lymph nodes, spleen, or liver.

In the Binet staging system, CLL is classified by the number of affected lymphoid tissue groups (neck lymph nodes, groin lymph nodes, underarm lymph nodes, spleen, and liver) and by whether or not the patient has anemia (too few red blood cells) or thrombocytopenia (too few blood platelets). Binet staging system divides CLL into 3 stages:

Binet stage A: Fewer than 3 areas of lymphoid tissue are enlarged, with no anemia or thrombocytopenia.

Binet stage B: 3 or more areas of lymphoid tissue are enlarged, with no anemia or thrombocytopenia.

Binet stage C: Anemia and/or thrombocytopenia are present.

The term "reference" as used herein refers to an average value of a control. The term "reference" also may refer to a standard gene or protein expression level.

The control sample refers to a sample of healthy subject/subjects.

As used herein, the term "level" refers to the degree of gene product expression in the biological sample.

As referred to herein, the term "treating" is directed to ameliorating symptoms associated with a disease, and lessening the severity or cure the disease.

The term "subject" refers to any mammalian subject. In some embodiments, the subject is a human subject.

The term "patient" as used herein refers to a subject that was diagnosed with CLL.

As used herein, the term "biological sample" refers to a sample obtained from a subject, including sample of biological tissue or fluid origin obtained in vivo or in vitro. Biological samples can be, without limitation, body fluid (e.g., blood, blood plasma, serum), organs, tissues, fractions and cells isolated from the subject/patient. Biological samples also may include sections of the biological sample including tissues (e.g., sectional portions of an organ or tissue). Biological samples may be dispersed in solution or may be immobilized on a solid support, such as in blots, assays, arrays, glass slides, microtiter, or ELISA plates.

Ectonucleotide pyrophosphatase/phosphodiesterase 4 (ENPP4; UniProt accession No.: Q9Y6X5) belongs to the enpp family which occupy a central role in purine signalling regulation by sequentially hydrolysing ATP to ADP and to adenosine. ENPP4 mRNA was found to differentially expressed in Osteosarcoma (OSA) metastatic cells (Mirreti et al. PLoS One. 2008 March 19; 3(3)). The aberrant expression of enpp family has been involved in cell motility and migration, angiogenesis, tumor cell invasion and bone mineralization dysfunction (Khanna et al., Cancer Res. 2001 May 1; 61(9):3750-9).

Alcohol dehydrogenase 5 (ADH5, aliases names: ADH-3, ADHX, FALDH, FDH, GSH-FDH, or GSNOR; UniProt accession No.: P11766) is a conserved enzyme for alcohol and aldehyde metabolism in mammals. The protein exhibits high activity for oxidation of long-chain primary alcohols and for oxidation of S-hydroxymethyl-glutathione. It was shown to be a negative regulator of neuronal differentiation.

Adenylate kinase 3 (AK3; aliases: AK3L1, AK6, AKL3L, AKL3L1, or FIX; UniProt accession No.: Q9UIJ7) is a GTP:ATP phosphotransferase that is found in the mitochondrial matrix. AK3 expression was found to be decreased in hepatocellular carcinoma (HCC) (Melle et al. J Proteome Res. 2007 January; 6(1):306-15). AK3 was suggested to be a mitotic inhibitor and that selected mitotic inhibitors may be useful for treating colon cancers or earlier lesions that have a high level of inflammatory cell infiltrate (Chopra Cancer Biol Ther. 2013 May; 14(5):436-49).

DEAD (Asp-Glu-Ala-Asp) box polypeptide 46 (DDX46; aliases: Prp5, PRPF5; UniProt accession No.: Q7L014) is a member of the DEAD box protein family. DEAD box proteins, characterized by the conserved motif Asp-Glu-Ala-Asp (DEAD), are putative RNA helicases. DDX46 protein expression is strongly increased in colorectal cancer (CRC) tissues compared to adjacent tissues. It was shown that DDX46 is critical for CRC cell proliferation and is a potential therapeutic target for CRC treatment (Li et al. Gene. 2015 Apr. 15; 560(2):237-44).

Adaptor-related protein complex 3, beta 1 subunit (AP3B1; aliases: PE, HPS, HPS2, ADTB3, or ADTB3A;

UniProt accession No.: O00203) is a protein that may play a role in organelle biogenesis associated with melanosomes, platelet dense granules, and lysosomes. The encoded protein is part of the heterotetrameric AP-3 protein complex which interacts with the scaffolding protein clathrin. Mutations in this gene are associated with Hermansky-Pudlak syndrome type 2.

Dehydrogenase/reductase (SDR family) member 4 (DHRS4; aliases: CR; NRDR; PHCR; PSCD; SDR-SRL; SDR25C1; SDR25C2; SCAD-SRL; UniProt accession No.: Q9BTZ2) is a peroxisomal member of the short-chain dehydrogenase/reductase superfamily.

Transducin (beta)-like 2 (TBL2; aliases: WBSCR13, WSbetaTRP; UniProt accession No.: Q9Y4P3) is a member of the beta-transducin protein family. Most proteins of the beta-transducin family are involved in regulatory functions. This protein is possibly involved in some intracellular signaling pathway.

Ribulose-5-phosphate-3-epimerase (RPE; alias: RPE2-1; UniProt accession No.: Q96AT9) catalyzes the reversible conversion of D-ribulose 5-phosphate to D-xylulose 5-phosphate. This reaction drives the nonoxidative phase of the pentose phosphate pathway (PPP), which generates precursors such as erythrose 4-phosphate, glyceraldehyde 3-phosphate, and fructose 6-phosphate that are necessary for the synthesis of aromatic amino acids and production of energy (Kruger et al., Curr. Op. Plant Biol. 6, 236-246).

Peptidylprolyl isomerase domain and WD repeat containing 1 (PPWD1; alias: KIAA0073; Uniprot accession No.: Q96BP3) is a putative peptidylprolyl isomerase (PPIase). PPIases accelerate the folding of proteins. It catalyzes the cis-trans isomerization of proline imidic peptide bonds in oligopeptides and may be involved in pre-mRNA splicing.

SNX18, or sorting nexin 18 (UniProt accession No.: Q96RF0), belongs to the sorting nexin (SNX) family, which contain a Phox homology (PX) domain, play crucial roles in regulating the intracellular membrane trafficking of the endocytic pathway.

IDH3A—isocitrate dehydrogenase 3 (P50213). Play a role in TCA cycle (mitochondria).

BRI3B-BRI3-binding protein (HCCRBP-1) (Q8WY22). Play a role in Outer mitochondrial membrane. BRI3B was found to induce tumorigenesis through p53 stabilization.

Methods of Measuring Expression Level

Comparing an expression level of a biomarker of the invention to its expression in a control sample or to a reference value comprises measuring and determining the expression level of the biomarker in a biological sample. Any method for detecting the marker expression as is known to a person skilled in the art may be used according to the teachings of the present invention. In some embodiments, the expression level can be measured by proteomic analysis methods as known in the art. Proteomics is the practice of identifying and quantifying the proteins, or the ratios of the amounts of proteins expressed in cells and tissues.

Those skilled in the art will be familiar with numerous specific immunoassay formats and variations thereof which may be useful for carrying out the method disclosed herein including enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, flow cytometry, immunohistochemistry, fluorescence microscopy, protein arrays, multiplexed bead arrays, magnetic capture, and in vivo imaging. See generally E. Maggio, Enzyme-Immunoassay, (1980) (CRC Press, Inc., Boca Raton, Fla.).

"Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," or "specifically interacts or binds" when referring to a protein or peptide (or other epitope), refers, in some embodiments, to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically, a specific or selective reaction will be at least twice background signal or noise and more typically more than 10 to 100 times background.

In some embodiments, the level of the biomarker is measured by contacting the biological sample with a specific antibody. A specific antibody may be for example a polyclonal antibody, a monoclonal antibody, a chimeric antibody, a human antibody, an affinity maturated antibody or an antibody fragment. While monoclonal antibodies are highly specific to a marker/antigen, a polyclonal antibody can preferably be used as a capture antibody to immobilize as much of the marker/antigen as possible.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen. If desired, the marker may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal. The antibodies are then obtained from blood samples taken from the animal. The techniques used to produce polyclonal antibodies are extensively described in the literature (see, e.g., Methods of Enzymology, "Production of Antisera with Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies.

Monoclonal antibodies (mAbs) may be readily prepared through use of well-known techniques, such as those exemplified in U.S. Pat. No. 4,196,265. Typically, this technique involves immunizing a suitable animal with a selected immunogen composition, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages but mice are preferred, with the BALB/c mouse being most preferred as this is most routinely used and generally gives a higher percentage of stable fusions.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

According to some embodiments, the level of the biomarker is measured by proteomic analysis. According to certain embodiments, the biomarker is measured by LC-MS/MS.

Nucleic Acid Testing (NAT) Assays

According to some embodiments, the methods of the invention comprise the comparing and/or detecting the expression level of genes.

Detection of a nucleic acid of interest in a biological sample may also optionally be effected by NAT-based assays, which involve nucleic acid amplification technology, such as PCR or variations thereof e.g. real-time PCR.

Amplification of a selected or target nucleic acid sequence may be carried out by a number of suitable methods. Numerous amplification techniques have been described and can be readily adapted to suit particular needs of a person of ordinary skill Non-limiting examples of amplification techniques include polymerase chain reaction (PCR), ligase chain reaction (LCR), strand displacement amplification (SDA), transcription-based amplification, the q3 replicase system and Nucleic acid sequence-based amplification (NASBA).

Kits

In some embodiments, the present invention provides an article of manufacture e.g., kit, such as an FDA approved kit, which contains diagnostic or prognosis reagents and instructions for use. The kit, in some embodiments, is accommodated by a notice associated with the container in a form prescribed by a regulatory agency regarding the manufacture, use or sale of pharmaceuticals, which notice is reflective of approval by the agency of the form of the compositions or human use.

According to some embodiments, the present invention provides a kit for diagnosing chronic lymphocytic leukemia, comprising: (i) at least one agent capable of detecting the expression level of at least one biomarker selected from the group consisting of DDX46, AK3, AP3B1, ADH5, BRI3B, IDH3A, SNX18, RPE, LTBP1, and PPWD1 in a biological sample; and (ii) means for comparing the expression level of the at least one biomarker in a sample obtained from a subject suspected to have CLL to the expression level of said at least one biomarker in a sample obtained from a healthy subject; or (iii) means for comparing the expression level of the at least one biomarker in a sample obtained from a subject suspected to have CLL to a reference value.

According to some embodiments, the kit comprises an agent capable of detecting the expression level of DDX46, AK3, AP3B1, and ADH5. According to some embodiments, the kit comprises an agent capable of detecting the expression level of DDX46 and AK3. According to some embodiments, the kit comprises an agent capable of detecting the expression level of PPWD1.

According to other embodiments, the present invention provides a kit for the prognosis of chronic lymphocytic leukemia state, comprising: (i) at least one agent capable of detecting the expression level of at least one biomarker selected from the group consisting of SNX18, DHRS4, TBL2, RPE, and ENPP4 in a biological sample; (ii) means for comparing the expression level of the at least one biomarker in a sample obtained from a subject suspected to have CLL to a reference value; and (iii) instruction material directing the correlation between the ratio of the at least one biomarker expression level to the reference level and the severity of the CLL.

The kits may include antibodies, protein arrays, reagents for use in immunoassays, protein controls, instruction sheets, gene expression database, and/or any means for determining and analyzing the expression level of the biomarkers according to the teachings of the invention.

According to an additional aspect, the present invention provides a kit for determining expression of at least one gene selected from the group consisting of DDX46, AK3, AP3B1, ADH5, BRI3B, IDH3A, SNX18, RPE, LTBP1, and PPWD1, comprising:
(i) a set of affinity reagents to specifically detect expression of said at least one gene, wherein said set of affinity reagents contains fewer than 1000 affinity reagents; and
(ii) at least one signal producing label attached directly or indirectly to the affinity reagent, said signal producing label being selected from the group consisting of a radioactive label, enzymatic labeling system, hapten, reporter dye and fluorescent label.

According to an additional aspect, the present invention provides a kit for determining expression of at least one gene selected from the group consisting of SNX18, DHRS4, TBL2, RPE, and ENPP4, comprising:
(i) a set of affinity reagents to specifically detect expression of said at least one gene, wherein said set of affinity reagents contains fewer than 1000 affinity reagents; and
(ii) at least one signal producing label attached directly or indirectly to the affinity reagent, said signal producing label being selected from the group consisting of a radioactive label, enzymatic labeling, hapten, reporter dye, and fluorescent label.

Method of Treating Chronic Lymphocytic Leukemia

According to an aspect, the present invention provides a method of treating chronic lymphocytic leukemia, comprising administering to a subject in need thereof, a therapeutically effective amount of at least one agent that reduces the expression or activity of at least one protein selected from the group consisting of AK3, DDX46, AP3B1, ADH5, BRI3B, IDH3A, PPWD1, SNX18, RPE, DHRS4, TBL2, NOP56, PSMC5, CTSS, APRT, PPP2R1A, CABIN1, HP1BP3, GCD, SLC25A1, RPL13A, UBE3A, MRPS22, and IGS20. Each possibility represents a separate embodiment of the invention.

According to some embodiments, the at least one protein is selected from the group consisting of DDX46 and AK3.

According to some embodiments, the agent is an interfering RNA molecule. In certain embodiments, the interfering RNA molecule is selected from the group consisting of a shRNA, a siRNA, and a miRNA.

In certain aspects, an interfering RNA of the invention has a length of about 19 to about 49 nucleotides. In other aspects, the interfering RNA comprises a sense nucleotide strand and an antisense nucleotide strand.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

Pharmaceutical Compositions

The agents of the present invention can be administered to a subject per se, or in a pharmaceutical composition where they are mixed with suitable carriers or excipients. Examples of suitable pharmaceutically acceptable carriers may include water, saline, PBS (phosphate buffered saline), dextrin, glycerol, and ethanol. The pharmaceutically acceptable carrier may be formulated for administration to a human subject or patient. The composition may be formulated into a dosage form which can release the active ingredient in a rapid or a sustained or delayed manner after administration.

According to some embodiments, the composition comprises as an active agent an interfering RNA molecule.

The interfering RNA molecule can be administered in a variety of methods as known in the art. Systemically administered RNA is rapidly cleared by the kidneys or liver due to its high solubility in water and negative charge. Therefore, according to some embodiments, the RNA is encapsulated. The encapsulation might enhance the circulation time of the RNA in the body and prevent degradation by extracellular nucleases. According to some embodiments, the pharmaceutical composition comprises a siRNA component and lipid component. According to certain embodiments, the interfering RNA molecule is administered within liposome. For example, WO2006113679 provides methods for the delivery of RNA interfering molecules to a cell via a neutral (non-charged) liposome. WO201011317 describes the use of amphoteric liposomal compositions for cellular delivery of small RNA molecules for use in RNA interference.

According to other embodiments, the interfering RNA molecule is administered directly or via a nucleic acid delivery system. The system may comprise a compound that stabilizes the RNA, such as a lipid or a protein. For example, WO1995022618 discloses a delivery system that contains a fusion protein having a target moiety and a nucleic acid binding moiety.

According to other embodiments, the composition comprises as an active agent at least one antibody specific to one biomarker according to the teachings of the invention.

The actual dosage amount of a composition of the present invention administered to a patient or subject can be determined by physical and physiological factors such as body weight, severity of condition, previous or concurrent therapeutic interventions, and on the route of administration. The practitioner responsible for administration will determine the concentration of active ingredient(s) in a composition and appropriate dose(s) for the individual subject.

EXAMPLES

Identification of Chronic Lymphocytic Leukemia Biomarkers.

Materials

Dulbecco's modified Eagle's medium (DMEM) supplemented with L-glutamine was purchased from Gibco (Grand Island, N.Y.). Fetal calf serum, penicillin-streptomycin, sodium pyruvate and nonessential amino acids were purchased from Biological Industries (Beit Haemek, Israel). Anti-actin monoclonal antibodies were from Millipore (Billerica, Mass.). Goat polyclonal anti-HK-I (sc-6517) and anti-HK-II (sc-6521) antibodies were obtained from Santa Cruz Biotechnology (Santa Cruz, Calif.). Rabbit polyclonal anti-BAX (PC66) and mouse monoclonal anti-Bcl-2 (0P60) antibodies were obtained from Calbiochem (Billerica, Mass.). Rabbit polyclonal anti-AIF (AF1457) antibodies were purchased from R&D Systems (Minneapolis, Minn.). Rabbit polyclonal anti-MAVS (ab-56230), rabbit polyclonal anti-VDAC1 (ab15895), rabbit polyclonal anti-SMAC/Diablo (ab-8115), anti-PPWD1 (ab-126710), anti-SLC25A1 (ab-99168), anti-DHRS4 (ab-68095), anti-UBE3A (ab-126765) and Cy2-conjugated anti-rabbit antibodies were obtained from Abcam (Cambridge, UK). Monoclonal anti-CD19 and CD5 antibodies were obtained from BD Bioscience (San Jose, Calif.). Horseradish peroxidase (HRP)-conjugated anti-mouse, anti-rabbit and anti-goat antibodies were from KPL (Gaithersburg, Md.).

Patients

Thirty one CLL patients from Soroka University Medical Center (14 males and 17 females with a median age of 69 years) were studied. CLL diagnosis was based on clinical examination, peripheral blood count and immuno-phenotyping (Table 3). Patients were not receiving any disease treatment, with 68% being at stage 0-1, 6% at stage 2 and 26% at stage 3-4. The research was approved by the Soroka University Medical center Advisory Committee on Ethics in Human Experimentation.

All of the experiments were conducted in accordance with national laws and regulations, the ethical principles set forth in the Declaration of Helsinki and with good clinical practice as described in the ICH guidelines. Written informed consent was obtained from all participants prior to entry into the study. All subjects received a copy of their signed and dated informed consent form.

Isolation of PBMC and CD19-Positive Cells

PBMCs were isolated from venous blood of CLL patients by Ficoll-Paque PLUS (GE Healthcare) density gradient centrifugation. After informed consent, venous blood (10-20 ml) was drawn from CLL patients or from normal adult donors. Blood was collected into heparin tubes and was diluted 1:1 with balance solution composed of solution A (1% D-glucose, 50 mM CaCl2, 0.98 mM MgCl2, 5.4 mM KCl and 0.145 M Tris-HCl, pH 7.6) and solution B (0.14 M NaCl) in a 1:9 ratio. The resulting mix was carefully layered on Ficoll-Paque Plus (10 ml of diluted blood on 15 ml Ficoll) in 50 ml conical tubes and centrifuged (400 g, 18-20° C., 40 min). The fine layer of mononuclear cells was transferred to a new centrifuge tube, washed thrice with balance solution and resuspended in culture medium appropriate to the application. The proportion of cancerous B cells in the total PBMC pool was analyzed by antibody-based detection of CD19/CD5 double positive cells and flow cytometry (Beckton-Dickinson, San Jose, Calif.).

CD19/CD5-positive cells were isolated from PMBCs using a magnetic bead-based method following the manufacturer's instructions, with minor modifications. Briefly, PMBCs ($2.5 \times 10^7$ cells) were centrifuged (300 g, 10 min), resuspended in 200 µl of buffer A (PBS, pH 7.2, 2 mM EDTA, 2% FBS), labeled with 50 µl of CD19 micro beads (Cat. No: 130-050-301, MACS Miltenyi biotech), mixed and incubated for 15 minutes at 4° C. The cells were washed with buffer A, centrifuged, resuspended in buffer A and subjected to magnetic separation with LS columns and a Midi MACS separator from MACS Miltenyi Biotech.

Cell Culture and Transfection

MEC-1 cells were grown in DMEM supplemented with 10% FBS, 1 mM L-glutamine, 100 U/ml penicillin, and 100 µg/ml streptomycin at 37° C. and 5% CO2. siRNAs were synthesized by Genepharma. Two siRNA sequences were used for each gene (sense (S) and anti-sense (AS) sequences). For siRNA-DDX46: (1) S: 1104-5'AAGUUGAUCUUCAGACAGCCCUU3'-1126 (SEQ ID NO:1) and AS: 5'AAGGGCUGUCUGAAGAUCAACUU3' (SEQ ID NO:2) and (2) S: 1320-5'AAUCCUGGGU-CCAGUGUGGAAUU3'-1342 (SEQ ID NO:3) and AS: 5'AAUUCCACACUGGACCCAGGAUU3' (SEQ ID NO:4). For siRNA-AK3: (1) S: 599-5'CAGAGACG-GUUAUCAAGAGACUAAA3'-623 (SEQ ID NO:5) and AS: 5'UUUAGUCUCUUGAUAACCGUCUCUG3' (SEQ ID NO:6) and (2) S: 704-5'CCAACAAGAUUUGGCCC-UAUGUAUA3'-728 (SEQ ID NO:7) and AS: 5'UAUA-CAUAGGGCCAAAUCUUGUUGG3' (SEQ ID NO:8). The scrambled siRNA used were S: 5'GCAAA-CAUCCCAGAGGUAU3' (SEQ ID NO:9) and AS: 5'AUACCUCUGGGAUGUUUGC3' (SEQ ID NO:10).

Cells were seeded in DMEM supplemented with 5% FBS (150,000 cells/well) in 6-well culture dishes to 40-60% confluence and transfected with 50 nM of the siRNA using the transfection reagent GeneTran III (Biomiga) according to the manufacturer's instructions.

Quantitative Real-Time PCR (qRT-PCR)

Total RNA was isolated from cells transfected with Scrambled siRNA, AK3 siRNA-1 and 2, DDX46 siRNA-1 and 2, AK3 1 and 2 siRNA, and DDX46 1 and 2 siRNA, or control cells using an RNeasy mini kit (Qiagen) according to the manufacturer's instructions. Total RNA quality was analyzed using the Agilent RNA 6000 nano kit. The RNA integrity values obtained for total RNA were 8-10. Complementary DNA was synthesized from 1 µg total RNA using a Verso cDNA synthesis kit (Thermo Scientific). Real-time fluorescent RT-PCR was performed using specific primers for DDX46 (forward—GCCCCAAACCAATTAAATCCTG (SEQ ID NO:11) and reverse—CAATGCCAAT-CAAATCTCGTCC (SEQ ID NO:12)) and AK3 (forward—TTACTGCTCGCTGGATTCATC (SEQ ID NO:13) and reverse—GTCTCTTGATAACCGTCTCTGG (SEQ ID NO:14)) (KiCqStart Primers; Sigma Aldrich) in triplicate, using Power SYBER green master mix (Applied Biosystems, Foster City, Calif.). The levels of the target genes were normalized relative to β-actin mRNA levels assessed using appropriate primers (forward—ACTCTTCCAGCCTTCCTTCC (SEQ ID NO:15), reverse—TGTTGGCGTACAGGTCTTTG (SEQ ID NO:16)). Samples were amplified by a 7300 Real Time PCR System (Applied Biosystems) for 40 cycles using the following PCR parameters: 95° C. for 15 seconds, 60° C. for 1 minute, and 72° C. for 1 minute. Copy numbers for each sample were calculated by the CT-based calibrated standard curve method. The means fold-change (±SEM) of the three replicates were calculated.

SRB Assay for Cell Proliferation

Forty-eight or 96 h post-transfection with siRNA, cells were washed twice with PBS, fixed with 10% trichloroacetic acid for 1-2 h, and subsequently stained with SRB. SRB was extracted from the cells using 100 mM Tris-base and absorbance at 510 nm was determined using an Infinite M1000 plate reader (Tecan, Männedorf, Switzerland).

Gel Electrophoresis and Immunoblotting

PBMCs isolated from CLL patients or healthy donors were resuspended in lysis buffer (50 mM Tris-HCl, pH 7.5, 150 mM NaCl, 1 mM EDTA, 1.5 mM MgCl2, 10% glycerol, 1% Triton X-100, a protease inhibitor cocktail (Calbiochem)), sonicated, centrifuged (17,500 g, 15 min, 4° C.) and samples (10-40 µg of protein) were subjected to SDS-PAGE. For immunostaining, gels were electrotransferred onto nitrocellulose membranes blocked with 5% non-fat dry milk and 0.1% Tween-20 in Tris-buffered saline and incubated overnight at 4° C. with the different primary antibodies, followed by incubation with the relevant HRP-conjugated secondary antibodies (1 h) and developed using enhanced chemiluminescence (Biological Industries). Band intensities were analyzed by densitometry using Multi Gauge software (Fujifilm). Readings were normalized to the intensities of β-actin signals that served as a loading control.

Assessment of Mitochondrial Mass

To measure mitochondria mass, cells were loaded with 20 nM MitoTracker Green (Molecular Probes) for 15 min at 37° C. and analyzed using flow cytometry.

Proteomics Analysis

PBMCs were solubilized in a lysis buffer (50 mM Tris-HCl, pH 7.5, 150 mM NaCl, 1 mM EDTA, 1.5 mM MgCl2, 10% glycerol, 1% Triton X-100, a protease inhibitor cocktail (Calbiochem)), followed by sonication and centrifugation (10 min, 600 g). Protein concentration of each lysate was determined using a BCA assay. Samples were then subjected to in-solution tryptic digestion as follows. Proteins were first reduced by incubation with 5 mM DTT for 30 min at 60° C., followed by alkylation with 10 mM iodoacetamide in the dark for 30 min at 21° C. Proteins were then subjected to digestion with trypsin (Promega; Madison, Wis.) at a 1:50 trypsin:protein ratio for 16 h at 37° C. Following digestion, detergents were cleared from the samples using commercial detergent removal columns (Pierce, Rockford, Ill.), and desalted using solid-phase extraction columns (Oasis HLB, Waters, Milford, Mass.). Digestions were stopped by addition of trifluroacetic acid (1%). The samples were stored at −80° C. until analysis.

LC-HR-MS/MS

For LC-HR-MS/MS, ULC/MS grade solvents were used for all chromatographic steps. Each sample was separated using split-less nano-ultra performance liquid chromatography columns (10 kpsi nanoAcquity; Waters, Milford, Mass.). The mobile phase was: (A) $H_2O$ and 0.1% formic acid, and (B) acetonitrile and 0.1% formic acid. Desalting of the samples was performed online using a reverse phase C18 trapping column (180 μm internal diameter, 20 mm length, 5 μm particle size; Waters). The peptides were then separated using a T3 HSS nano-column (75 μm internal diameter, 250 mm length, 1.8 μm particle size; Waters) at 0.3 μL/min. Peptides were eluted from the column into the mass spectrometer using the following gradient: 4% to 35% (B) for 150 min, 35% to 90% (B) for 5 min, maintained at 90% for 5 min and then back to initial conditions. The nano-UPLC was coupled online through a nano-ESI emitter (10 μm tip; New Objective; Woburn, Mass.) to a quadrupole Orbitrap mass spectrometer (Q Exactive, Thermo Scientific) using a FlexIon nanospray apparatus (Proxeon). Data was acquired in the DDA mode, using a Top12 method (Kelstrup et al., J Proteome Res. 2012; 11(6):3487-97.). Raw data was imported into Expressionist software (Genedata) (Ueda et al., PLoS One. 719 2011; 6(4):e18567). The software was used for retention time alignment and peak detection of precursor peptide intensities. A master peak list was generated from all MS/MS events and sent for database searching using Mascot v2.4 (Matrix Sciences). Data was searched against a database containing forward and reverse human protein sequences from UniprotKB-SwissProt, and 125 common laboratory contaminants, totaling 20,304 entries. Fixed modification was set to carbamidomethylation of cysteines, while variable modification was set to oxidation of methionines. Search results were then imported back to Expressionist for annotation of detected peaks. Identifications were filtered such that the global false discovery rate was a maximum of 1%. Protein abundance was calculated based on the three most abundant peptides.

Two independent LC-HR-MS/MS analyses of healthy donors and CLL patients were performed, with six healthy donors and nineteen CLL patients, and five age-matched healthy donors and nine CLL patients, were used in the first and second analysis, respectively. Proteins with at least one unique peptide identified were used for further analysis.

Statistics and Bio-Informatics Analyses

Means±SEM of results obtained from indicated independent experiments are presented. The level of significance of differences between control (healthy) and experimental (CLL patients) groups or non-treated CLL patients (Group A) and treated CLL patients (Group B) was determined using the non-parametric Mann-Whitney U test. A difference was considered statistically significant when the P value was deemed<0.05 (*), <0.01 () or <0.001 (*). Statistics for data analysis were computed using the SPSS statistical package, version 17.0. A non-parametric receiver operating characteristic (ROC) curve was plotted and the area under the ROC curve (AUC) was estimated, indicating the probability of the protein to be a valid diagnostic marker, with values ranging from 0 to 1, where 1 indicates a perfect marker. LC-HR-MS/MS data were imported into Partek Genomics Suite software (Partek, St. Louis, Mo.) and difference between expression levels of the proteins in the different groups was calculated using the one-way analysis of variance (ANOVA). Functional enrichment analysis of significantly different proteins was performed using DAVID bioinformatics resources v6.7 (Huang et al., Nature protocols. 2009; 4:44-57). Kaplan-Meier survival curves were constructed to compare survival between CLL patients with high and low expression levels of the indicated protein. P<0.05 was taken to indicate a statistically significant difference.

Example 1: Protein Profiling in PBMCs from CLL Patients and Healthy Donors

PBMCs isolated from healthy donors and CLL patients receiving no disease treatment were analyzed using LC-HR-MS/MS and immunoblotting to explore possible CLL biomarkers and disease progression predication. PBMC samples were collected from six healthy individuals and nineteen CLL patients. Hierarchical clustering based on the protein expression pattern clearly allowed for distinction between the healthy donors and the CLL patients, with the expression level of 1,360 proteins being changed (fold change (FC)≥121 and p-value<0.01, of which 118 with a FC≥100).

Next, functional analysis of proteins differentially expressed between healthy donors and CLL patients was performed using the DAVID tool based on the KEGG databases (Kanehisa M et al., Nucleic Acids Res. 2000; 28(1):27-30; Kanehisa M et al., Nucleic Acids Res. 2014, 42:D199-205; Ashburner M et al., Nature genetics. 2000; 25:25-9; Consortium TGO. Nucleic Acids Res. 2015; 43:D1049-56). The analysis revealed enrichment for biological pathways related to metabolism, the immune system and protein synthesis and degradation, as well of proteins belonging to the mitochondria, RNA splicing and translation functional groups (or associated functions). Remarkably, proteins having mitochondria-related functions were highly enriched in both analyses, including proteins involved in apoptosis and metabolism. Similarly, enrichment of RNA splicing proteins, where mutations were shown to be indicative of high-risk in CLL patients, was seen (Rossi D et al., Expert Rev Hematol. 2012; 5(6):593-602; Wang et al., N Engl J Med. 2011, 365(26):2497-506). These results indicate the validity of the MS analysis, which was thus used for further analysis.

Example 2: Identification of Novel Bio-Markers for CLL

To further select proteins for continued focus, the LC-HR-MS/MS analysis was repeated using 14 samples (from five age-correlated healthy donors and nine CLL patients) that included new as well as previously analyzed samples. This narrowed the focus to 59 proteins that presented a clear common expression pattern in both LC-HR-MS/MS analyses. These proteins include several proteins that have previously been identified as being mutated in CLL or proposed as CLL diagnosis and prognosis markers (Table 1). A protein that induces tumorigenesis through p53 stabilization but was not previously found to correlated with CLL is a putative peptidylprolyl isomerase (PPlase, PPWD1) that accelerates the folding of proteins and may be involved in pre-mRNA splicing. FIG. 1 demonstrates that PPWD1 protein expression is highly elevated in CLL patients.

Figure 2:
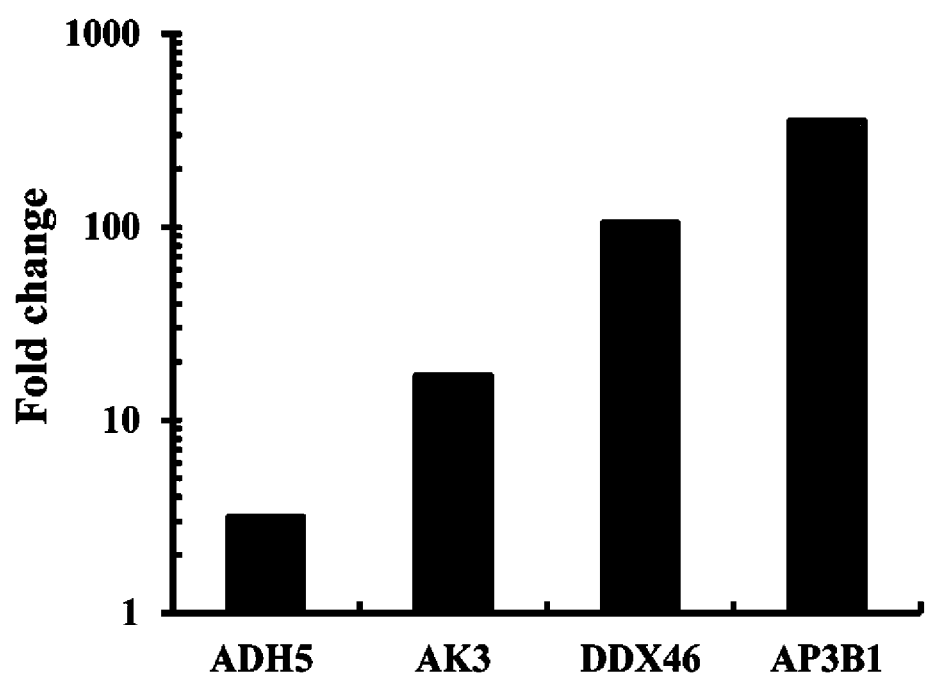
FIG. 2 shows the fold of increase in ADH5, AK3, DDX46, and AP3B1 protein expression levels in CLL patients compared to healthy individual. MS/MS analysis.

Several proteins whose expression levels were significantly different between healthy and CLL patients were not previously reported to be associated with cancer, including CLL. These include AP3B1, which involved in the biogenesis of late endosomal/lysosomal structures (Di Pietro et al., Mol Biol Cell. 2006; 17(9):4027-38.), DDX46 RNA helicase, involved in pre-mRNA processing (Linder et al., Nat Rev Mol Cell Biol. 2011; 12(8):505-16), alcohol dehydrogenase 5 (ADH5) involved in the metabolism of alcohols and aldehydes (Hoog J O, et al., 2001; 8(1):71-6.), and the mitochondrial protein adenylate kinase 3 (AK3), involved in maintaining the homeostasis of cellular nucleotides (Noma T, et al., Biochem J. 2001, 15; 358(Pt 1):225-32)(Table 1; FIG. 2).

Figure 3:
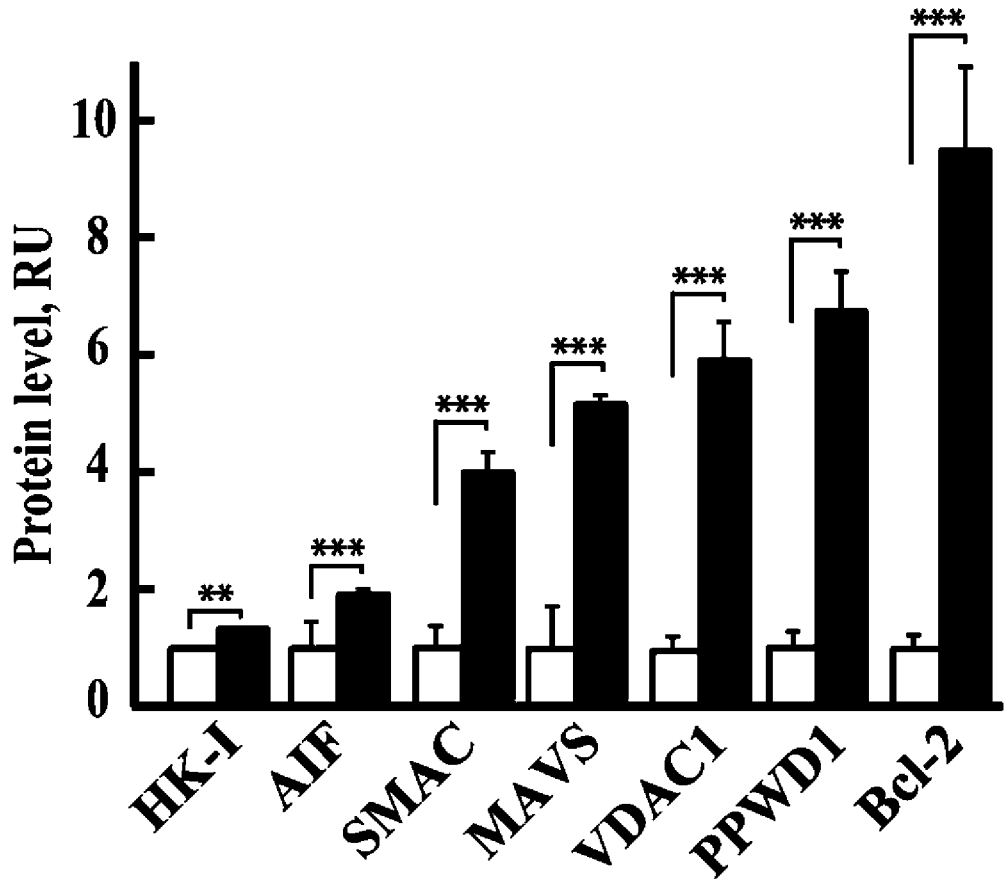
FIG. 3 shows over-expression of Bcl-2, VDAC1, AIF, MAVS, SMAC/Diablo and PPWD1 in PBMCs from CLL patients. Cell lysates of PBMCs derived from CLL patients and healthy donors were probed with antibodies directed against Bcl-2, VDAC, AIF, MAVS, SMAC/Diablo, HK-1 and PPWD1. Quantitative analysis of protein levels of healthy donors (white) and CLL patients (black) based on immunoblot assays is presented. $P<0.001$ (*) or $P<0.01$ (), as determined by the Mann-Whitney test.
Figure 4A:
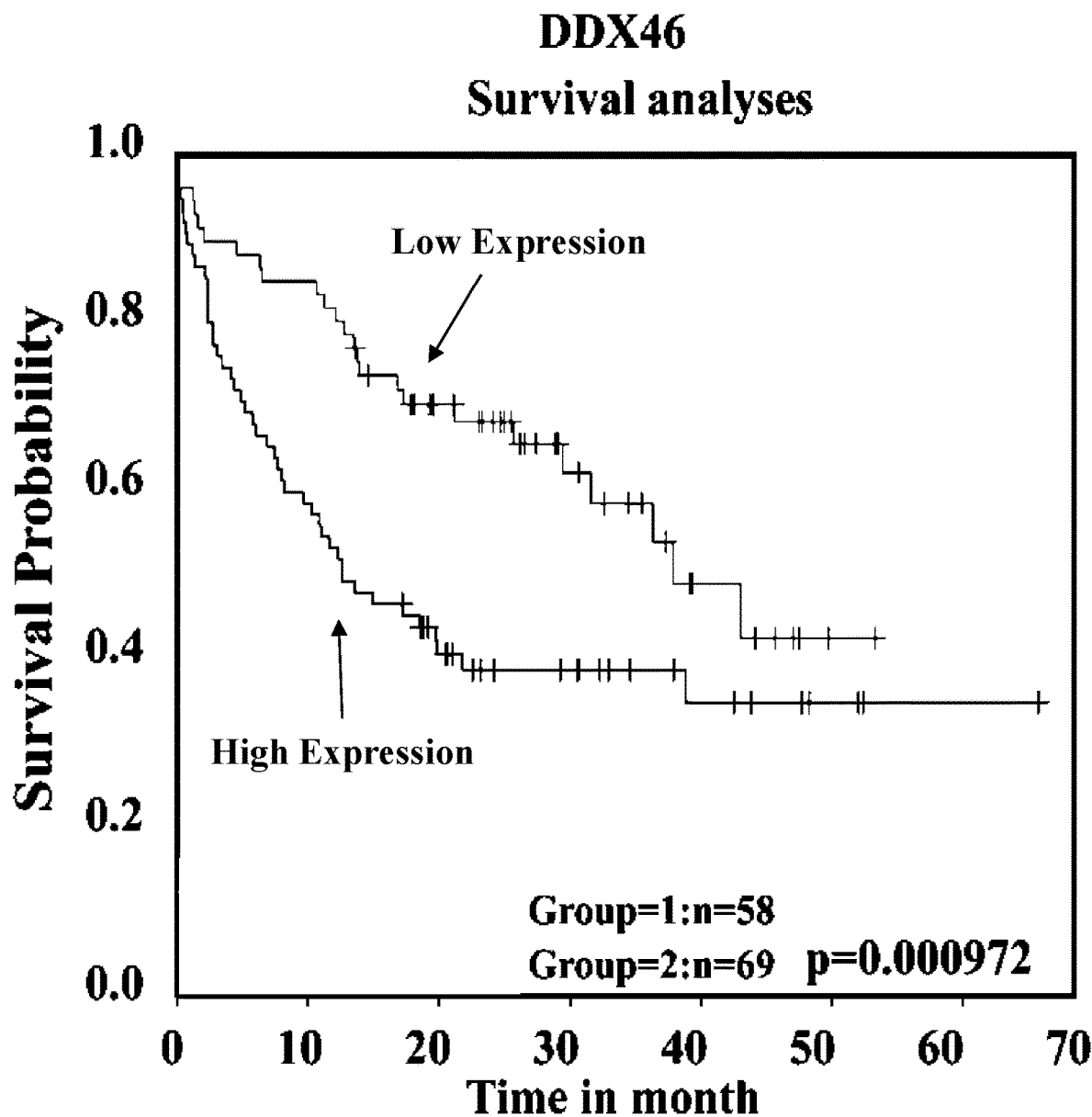
FIGS. 4A-4D show the prognostic value of DDX46, AK3, ADH5, and AP3B1 levels in CLL patients. Kaplan-Meier survival curves for CLL patients are presented for patients with high expression and low expression as indicated for DDX46 (FIG. 4A), AK3 (FIG. 4B), ADH5 (FIG. 4C), and AP3B1 (FIG. 4D). Tick marks represent the survival time for patients that did not participate in the full duration of the experiment. Survival time was measured from date of diagnosis to date of death for patients who died and to the date of the last follow-up for those who were alive at the time of the analysis. A difference between two curves was considered statistically significant when $P<0.05$.
Figure 4B:
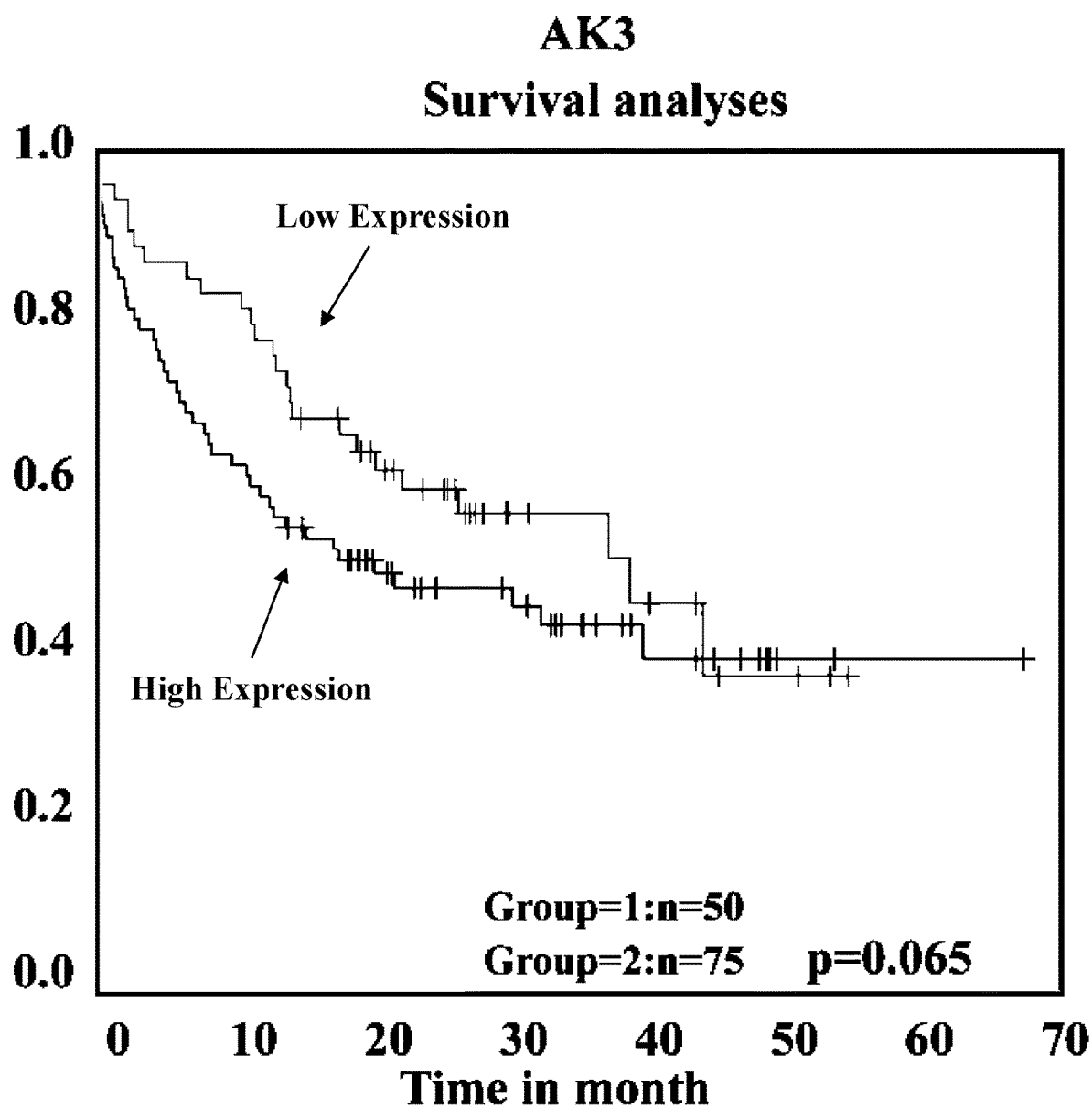
Figure 4C:
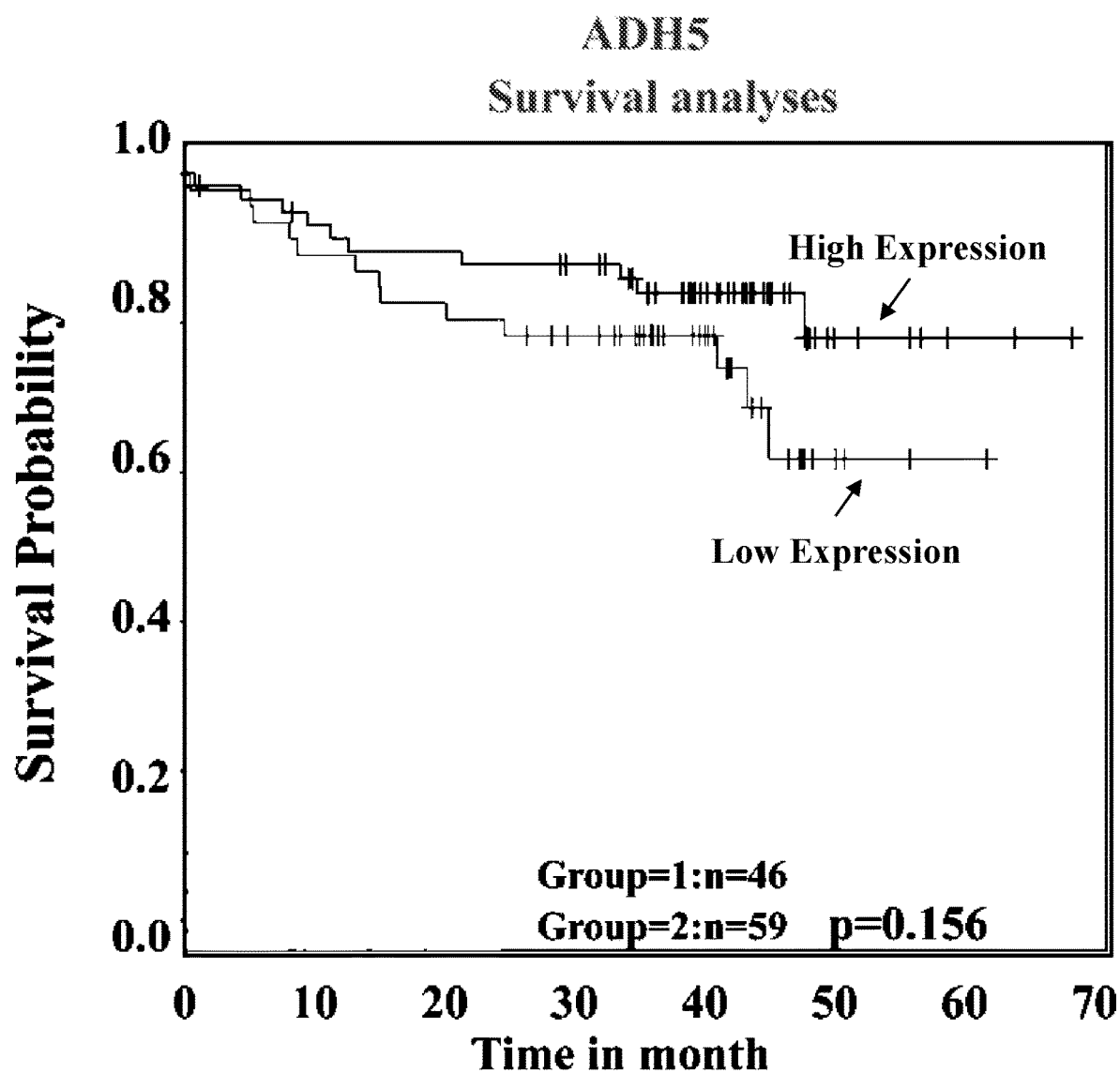
Figure 4D:
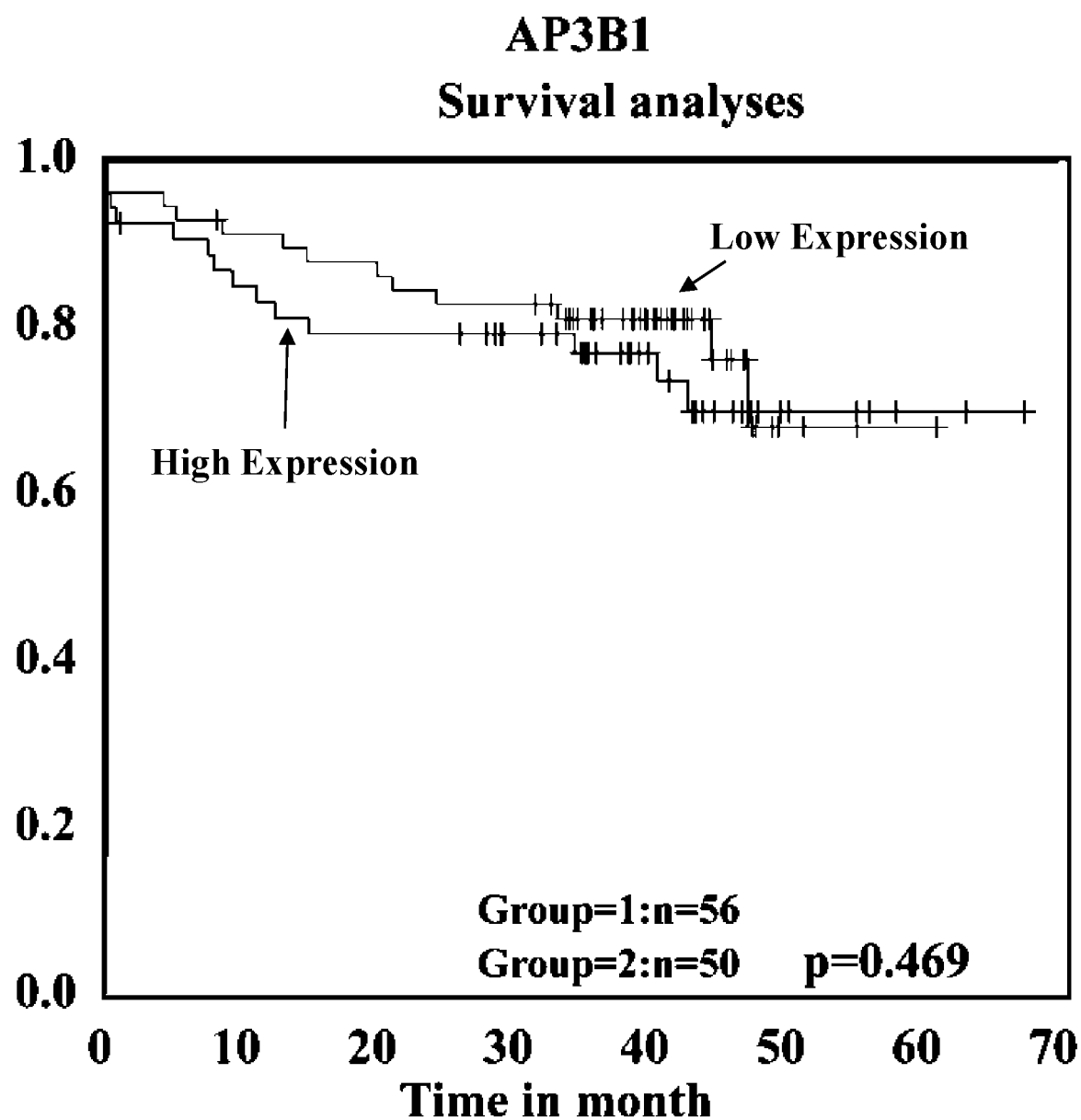

Over-expression of Bcl-2, VDAC1, AIF, MAVS, SMAC/Diablo and PPWD1 in PBMCs from CLL patients is shown in FIG. 3. Cell lysates of PBMCs derived from CLL patients and healthy donors were probed with antibodies directed against Bcl-2, VDAC, AIF, MAVS, SMAC/Diablo and PPWD1. Quantitative analysis of protein levels of healthy donors (white) and CLL patients (black) based on immunoblot assays is presented. $P<0.001$ (*) or $P<0.01$ (), as determined by the Mann-Whitney test.

To further test the prognostic value of AP3B, ADH5, DDX46 and AK3 proteins in CLL, Kaplan-Meier survival analysis was performed on public available gene expression data. A set of CLL patients in which the percent of patients surviving with high mRNA levels was compared to the survival of patients with low mRNA levels. Significant difference between the two patient groups was found for DDX46 ($p=0.00097$) but not for AP3B1 ($P=0.469$), ADH5 ($P=0.156$) and AK3 ($P=0.065$) (FIGS. 4A-4D). Data analysis was performed with the DRUGSURV bioinformatics analysis tool (http://www.bioprofiling.de/GEO/DRUGSURV).

Figure 5:
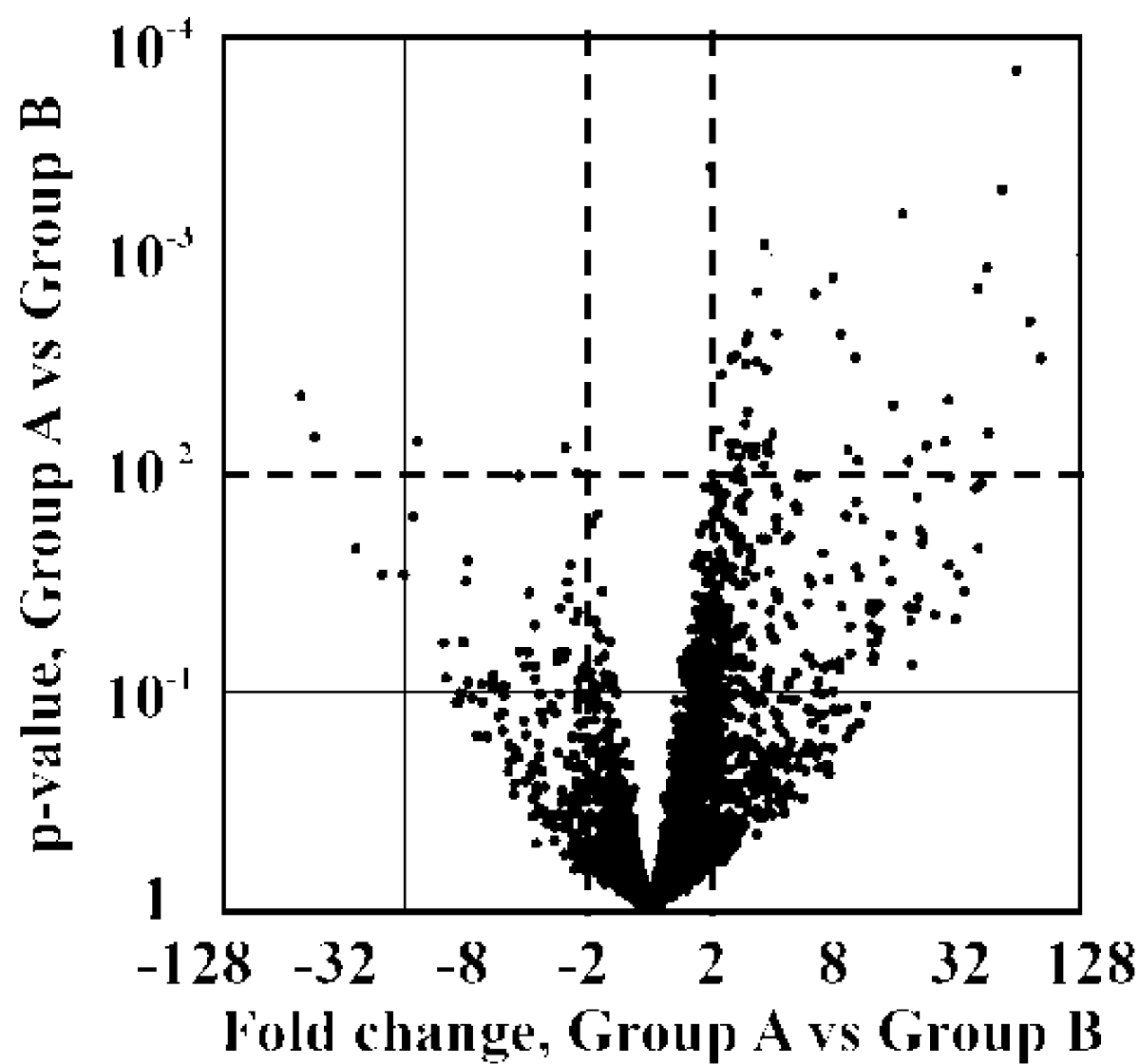
FIG. 5 is a volcano plot that shows proteins expression (proteomics analysis) comparison between CLL patients in a stable disease state (group A) and patients transferred to anti-cancer treatments (group B). Presented are p-values and the magnitude of the difference in expression values (fold change) between groups B and A. Dash lines indicate a nominal p-value cutoff of 0.01 and a fold change cutoff of |2|. Fifty proteins passed the cutoff values of p-value<0.01 and FC≥|2|.
Figure 6:
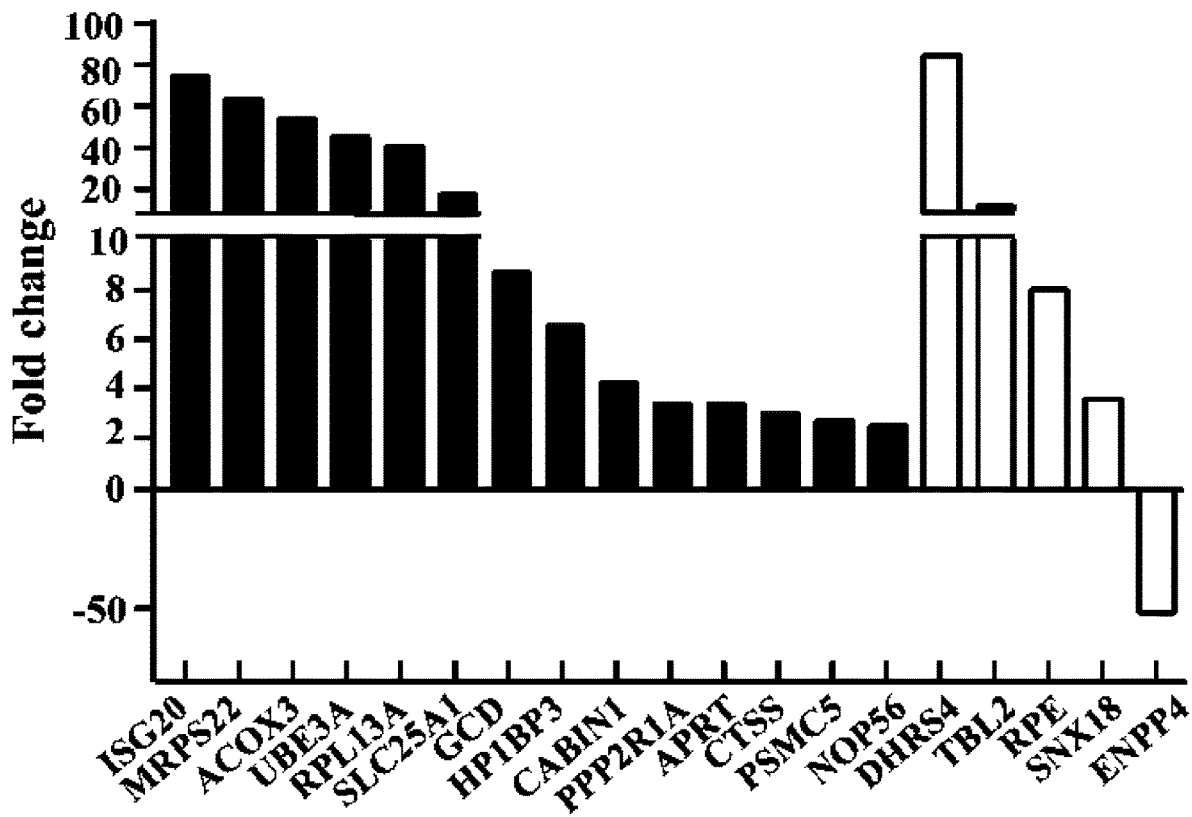
FIG. 6 shows differentially expressed proteins between groups A and B (p-value<0.01, FC≥|2|), divided as proteins reported to be associated (black) or not associated (white) with cancer.
Figure 7:
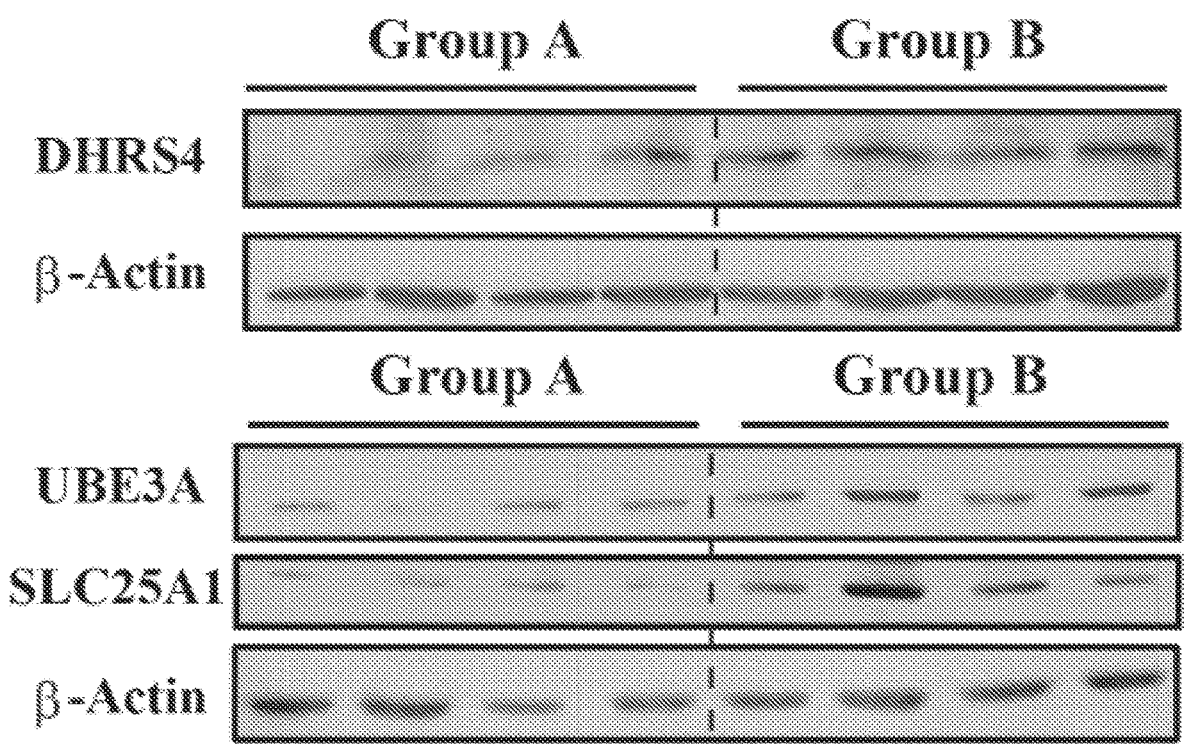
FIG. 7 shows representative immunoblots that show the expression levels of DHRS4, UBE3A, and SLC25A1 in patients from groups A and B. Actin was used as loading control.

Example 3: Proteomics Analysis Allows Distinction Between Patients in a Stable Disease State and Those Transferred to Anti-Cancer Treatment or Who Died Of the PBMCs derived from 19 CLL patients subjected to LC-HR-MS/MS analysis, 10 patients were in a stable disease state and needed no treatment 2-3 years after blood samples were obtained. Nine patients were subjected to treatment or died 0.5 to 36 months after collection of blood samples. Thus, to further identify proteins that allow to distinguish between patients in a stable disease state (group A) from those transferred to anti-cancer treatment or who died (group B), the protein expression profile of these two groups was analyzed. Hierarchical clustering of all 19 CLL samples could not properly separate between groups A and B. Yet, a volcano chart derived from a t-test with equal variances analysis revealed 50 proteins whose expression levels were significantly different between the two groups ($FC \geq |2|$, p-value<0.01) (FIG. 5). Nineteen of the 50 proteins are presented with their fold change between groups A and B, their proposed function, and subcellular localization (Table 2, FIG. 6). These include proteins that were previously associated with different types of cancer, of which mutation in one of them (ACOX3) was highly associated with a prediction of CLL outcome, while five proteins had no report connecting them to cancer. The results were further verified by immunoassay. As shown in FIG. 7, the expression of DHRS4, UBE3A, and SLC25A1 proteins was elevated in patients that were later received anti-cancer treatments or their disease state was worsen (group B) as compared to CLL patients in a stable disease state.

TABLE 1

List of selected proteins differentially expressed between healthy donors and CLL patients identified by LC-HR-MS/MS. Two independent LC-HR-MS/MS experiments were performed as described in the Materials and Methods section. From each experiment, differentially expressed proteins (p-value < 0.01, FC ≥ |2|) were filtered and proteins differentially expressed in both experiments were selected. Proteins of relevance to CLL or with potential as biomarkers are listed. For each protein, the name, fold change and p-value in each experiment, as well as its function, subcellular localization and relevance to cancer are indicated. Proteins were divided into three groups based on their known association to CLL, relation to metabolism or potential as metabolism-unrelated biomarkers for CLL.

| Protein (UniProt accession) LC-HR-MS/MS analysis: | Fold change/ P value 1$^{st}$ | 2$^{st}$ | Proposed function (cell localization) |
|---|---|---|---|
| SNX18-sorting nexin 18 (Q96RFO) | 5.15 $1.04 \times 10^{-3}$ | — | Endocytosis and vesicle trafficking during interphase and at the end of mitosis (cell membrane) |
| RPE-ribulose-5-phosphate-3-epimerase (Q96AT9) | 7.71 $9.29 \times 10^{-3}$ | — | Pentose phosphate pathway (cytoplasm) |
| BCL-2-B cell lymphoma 2 (P10415) | 24.5 $1.1 \times 10^{-7}$ | 6.4 $3.4 \times 10^{-3}$ | Suppresses apoptosis |

TABLE 1-continued

List of selected proteins differentially expressed between healthy donors and CLL patients identified by LC-HR-MS/MS. Two independent LC-HR-MS/MS experiments were performed as described in the Materials and Methods section. From each experiment, differentially expressed proteins (p-value < 0.01, FC ≥ |2|) were filtered and proteins differentially expressed in both experiments were selected. Proteins of relevance to CLL or with potential as biomarkers are listed. For each protein, the name, fold change and p-value in each experiment, as well as its function, subcellular localization and relevance to cancer are indicated. Proteins were divided into three groups based on their known association to CLL, relation to metabolism or potential as metabolism-unrelated biomarkers for CLL.

| Protein (UniProt accession) LC-HR-MS/MS analysis: | Fold change/ P value $1^{st}$ | $2^{st}$ | Proposed function (cell localization) |
|---|---|---|---|
| IGHD—immunoglobulin heavy constant delta | 44.2 $2.3 \times 10^{-6}$ | >1000 $2.1 \times 10^{-13}$ | Major antigen receptor on the surface of B-cells (secreted, plasma membrane) |
| KSYK-spleen tyrosine kinase (P43405) | 6.8 $7.5 \times 10^{-6}$ | 4.0 $2.4 \times 10^{-4}$ | Mediates signal transduction (plasma membrane, cytoplasm) |
| NFKB2-NF-kappa-B p100 (Q00653) | 21.6 $3.1 \times 10^{-6}$ | 21.6 $3.1 \times 10^{-6}$ | Transcription factor, involves in inflammation, immunity, differentiation, tumorigenesis and apoptosis (nucleus, cytoplasm) |
| CD74-HLA class II histocompatibility antigen gamma chain (P04233) | 5.1 $1.7 \times 10^{-4}$ | 5.1 $4.5 \times 10^{-5}$ | MHC class II antigen processing (plasma membrane) |
| VDAC1-voltage dependent anion channel 1 (P21796) | 5.3 $2.8 \times 10^{-5}$ | 4.8 $4.8 \times 10^{-4}$ | Ions and metabolites transport. Involves in apoptosis (OMM, plasma membrane) |
| VDAC2-voltage dependent anion channel 2 (P45880) | 3.1 $1.4 \times 10^{-3}$ | 4.5 $7.4 \times 10^{-4}$ | Transport of ions and metabolites (OMM) |
| AIF-apoptosis inducing factor | 10.6 $3.6 \times 10^{-9}$ | — | Initiator of apoptosis (mitochondria, in apoptosis translocates to nucleus) |
| IDH3A-isocitrate dehydrogenase 3 (P50213) | 2.6 $7.1 \times 10^{-3}$ | 6.8 $9.6 \times 10^{-5}$ | TCA cycle (mitochondria) |
| ADH5-alcohol dehydrogenase 5 (P11766) | 2.8 $8.1 \times 10^{-4}$ | 3.5 $7.8 \times 10^{-4}$ | Oxidation of alcohols and aldehydes, (cytoplasm) |
| AK3-adenylate kinase 3 (Q9UL17) | 29.9 $3.0 \times 10^{-5}$ | 4.1 $1.9 \times 10^{-3}$ | Maintaining the homeostasis of cellular nucleotides (mitochondria) |
| BRI3B-BRI3-binding protein (HCCRBP-1) (Q8WY22) | 5.8 $2.9 \times 10^{-5}$ | 389.4 $2.7 \times 10^{-3}$ | Outer mitochondrial membrane |
| PPWD1-peptidylprolyl isomerase domain and WD repeat containing 1 (Q96BP3) | 35.7 $9.7 \times 10^{-5}$ | 105.4 $7.7 \times 10^{-3}$ | Accelerates the folding of proteins, possibly involved in pre-mRNA splicing (nucleus) |
| GELS-gelsolin (P06396) | −3.3 $4.3 \times 10^{-3}$ | −5.0 $4.0 \times 10^{-3}$ | Actin modulating protein (secreted, cytoplasm) |
| DDX46-DEAD box protein 46 (Q7L014) | 9.1 $1.9 \times 10^{-5}$ | 201.4 $1.2 \times 10^{-3}$ | Pre-mRNA processing (nucleus) |
| LTBP1-latent TGFβ binding protein 1 (Q14766) | −4.7 $1.6 \times 10^{-5}$ | −6.2 $7.9 \times 10^{-3}$ | Associates with pro-TGFβ complex. Modulates TGFβ activity (secreted) |
| AP3B1-AP-3 complex subunit beta-1 (O00203) | 9.6 $1.7 \times 10^{-4}$ | 698.8 $8.5 \times 10^{-5}$ | Biogenesis of late endosomal/ lysosomal structures (Golgi membrane) |

TABLE 2

List of selected proteins differentially expressed between CLL patients in a stable disease state and those transferred to anti-cancer treatments, identified by LC-HR-MS/MS. Differentially expressed proteins between CLL patients in a stable disease state and those transferred to anti-cancer treatments (p-value < 0.01, FC ≥ |2|) were filtered and proteins of interest are presented based on their relevance to cancer and potential as biomarkers. For each protein, its name, fold change and p-value are indicated, as are its function, subcellular localization and relevance to cancer.

| Protein (UniProt accession) | Fold change/ P value | Proposed function and cellular localization |
|---|---|---|
| DHRS4-dehydrogenase/reductase (SDR family) member 4 (Q9BTZ2) | 84.5<br>$3.0 \times 10^{-3}$ | Reduces all-trans-retinal and 9-cis retinal (peroxisome) |
| ISG20-interferon stimulated exonuclease gene 20kDa (Q96AZ6) | 74.6<br>$2.0 \times 10^{-3}$ | Exhibit antiviral activity against RNA viruses (nucleus, cytoplasm) |
| MRPS22-mitochondrial ribosomal protein S22 (P82650) | 63.8<br>$1.4 \times 10^{-4}$ | Protein synthesis (mitochondria) |
| ACOX3-acyl-coenzyme A oxidase 3 (O15254) | 54.2<br>$5.0 \times 10^{-4}$ | Fatty acid beta-oxidation (peroxisome) |
| ENPP4-ectonucleotide pyrophosphatase/phosphodiesterase 4 (Q9Y6X5) | −51.8<br>$4.4 \times 10^{-3}$ | Hydrolyze phosphodiester bonds, act as a procoagulant (cell membrane) |
| UBE3A-ubiquitin protein ligase E3A (Q05086) | 45.5<br>$1.1 \times 10^{-3}$ | Targeting proteins for degradation (cytoplasm) |
| RPL13A-60S ribosomal protein L13a (P40429) | 41.0<br>$1.4 \times 10^{-3}$ | Associated with ribosomes but not with the canonical ribosome function, having extra-ribosomal functions (cytoplasm) |
| SLC25A1-solute carrier family 25, member 1 (P53007) | 17.5<br>$6.4 \times 10^{-4}$ | Citrate transporter (mitochondria) |
| TBL2-transducin (beta)-like 2 (Q9Y4P3) | 10.3<br>$2.9 \times 10^{-3}$ | Associate with triglyceride metabolism (ER) |
| GCD-glutaryl-Coenzyme A dehydrogenase (Q92947) | 8.7<br>$2.3 \times 10^{-3}$ | Involved in the degradation of L-lysine, L-hydroxylysine, and L-tryptophan (mitochondria) |
| RPE-ribulose-5-phosphate-3-epimerase (Q96AT9) | 8.0<br>$1.3 \times 10^{-3}$ | Pentose phosphate pathway (cytoplasm) |
| HP1BP3-heterochromatin protein 1, binding protein 3 (Q5SSJ5) | 6.5<br>$1.5 \times 10^{-3}$ | Maintains heterochromatin integrity during G1/S progression (nucleus) |
| CABIN1-calcineurin binding protein1 (Q9Y6J0) | 4.2<br>$2.3 \times 10^{-3}$ | Inhibits calcineurin-mediated signal transduction (nucleus) |
| SNX18-sorting nexin 18 (Q96RF0) | 3.6<br>$8.9 \times 10^{-4}$ | Endocytosis and vesicle trafficking during interphase and at the end of mitosis (cell membrane) |
| PPP2R1A-Protein Phosphatase 2, Regulatory Subunit A, Alpha (P30153) | 3.4<br>$1.5 \times 10^{-3}$ | Regulation of cell adhesion; second-messenger-mediated signaling; mitotic nuclear envelope reassembly and more (cytoplasm) |
| APRT-adenine phosphoribosyl-transferase (P07741) | 3.4<br>$3.1 \times 10^{-3}$ | Involved in purine salvage pathway resulting in the formation of AMP (cytoplasm) |
| CTSS-cathepsin S (P25774) | 3.0<br>$2.5 \times 10^{-3}$ | Protease in MHC-II- mediated antigen presentation (lysosome) |
| PSMC5-proteasome (prosome, macropain) 26S subunit, ATPase 5 (also known as S8; p45; SUG1; TBP10; TRIP1) (P62195) | 2.7<br>$2.9 \times 10^{-3}$ | ATP-dependent degradation of ubiquitinated proteins (cytoplasm) |
| NOP56-Nuclear protein 56 (O00567) | 2.5<br>$3.0 \times 10^{-3}$ | Involved in the 60S ribosomal subunit biogenesis (nucleus) |

Example 4: Silencing of DDX46 or AK3 mRNAs Reduces Growth of MEC-1 Cells

Figure 8A:
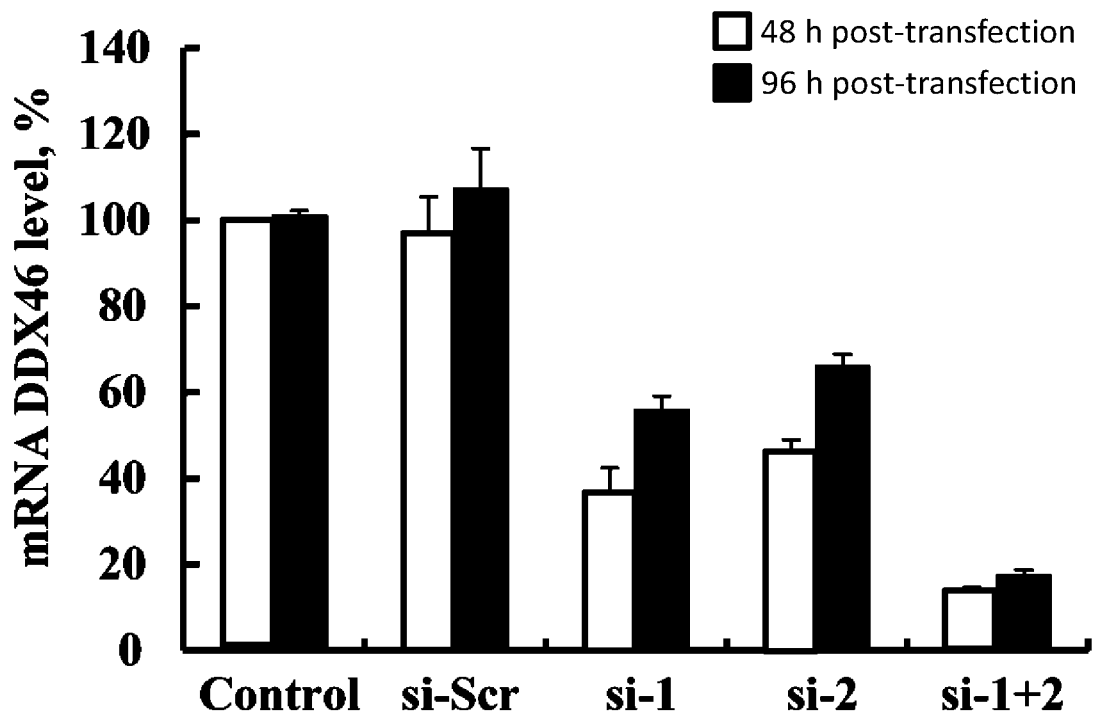
FIGS. 8A-8C show that siRNA silencing of AK3 or DDX46 expression inhibits cell growth. MEC-1 cells were transfected with (50 nM) scrambled siRNA (si-Scr), one of the 2 different siRNAs against AK3 (siAK3 1 or 2), or against DDX46 (siDDX46 1 or 2), a combination of siAK3 1 and 2 or a combination of siDDX46 1 and 2 and, at the indicated time, were analyzed for AK3 and DDX46 mRNA levels by RT-PCR (FIGS. 8A and 8B) or analyzed for cell growth using the SRB method (n=3) (FIG. 8C).
Figure 8B:
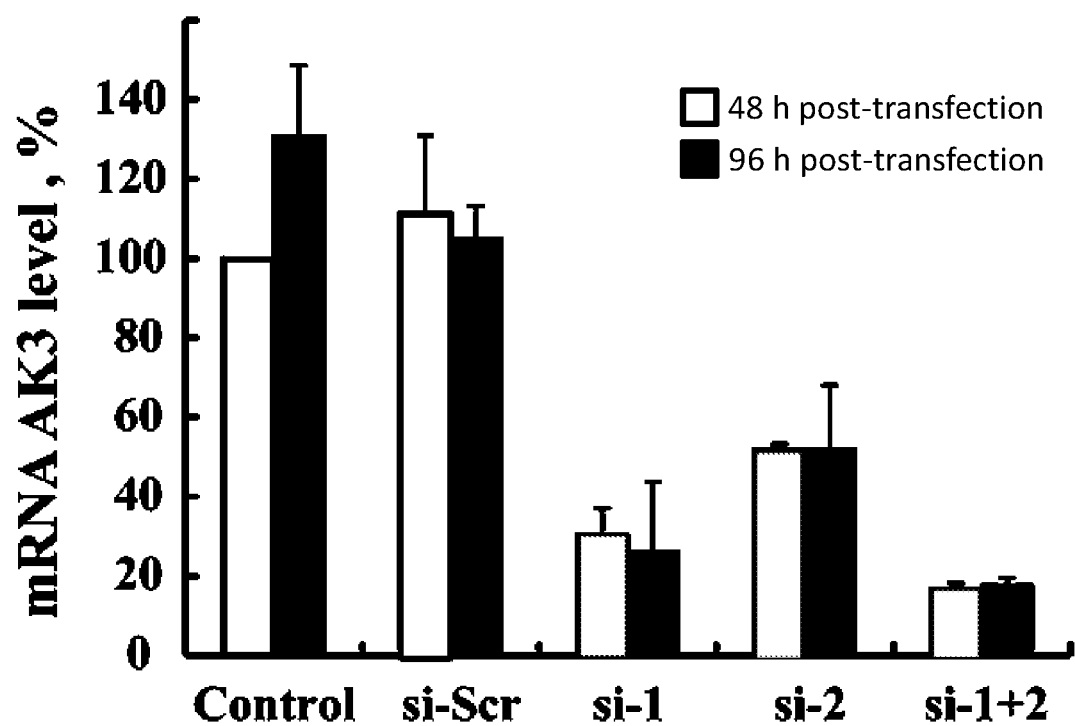
Figure 8C:
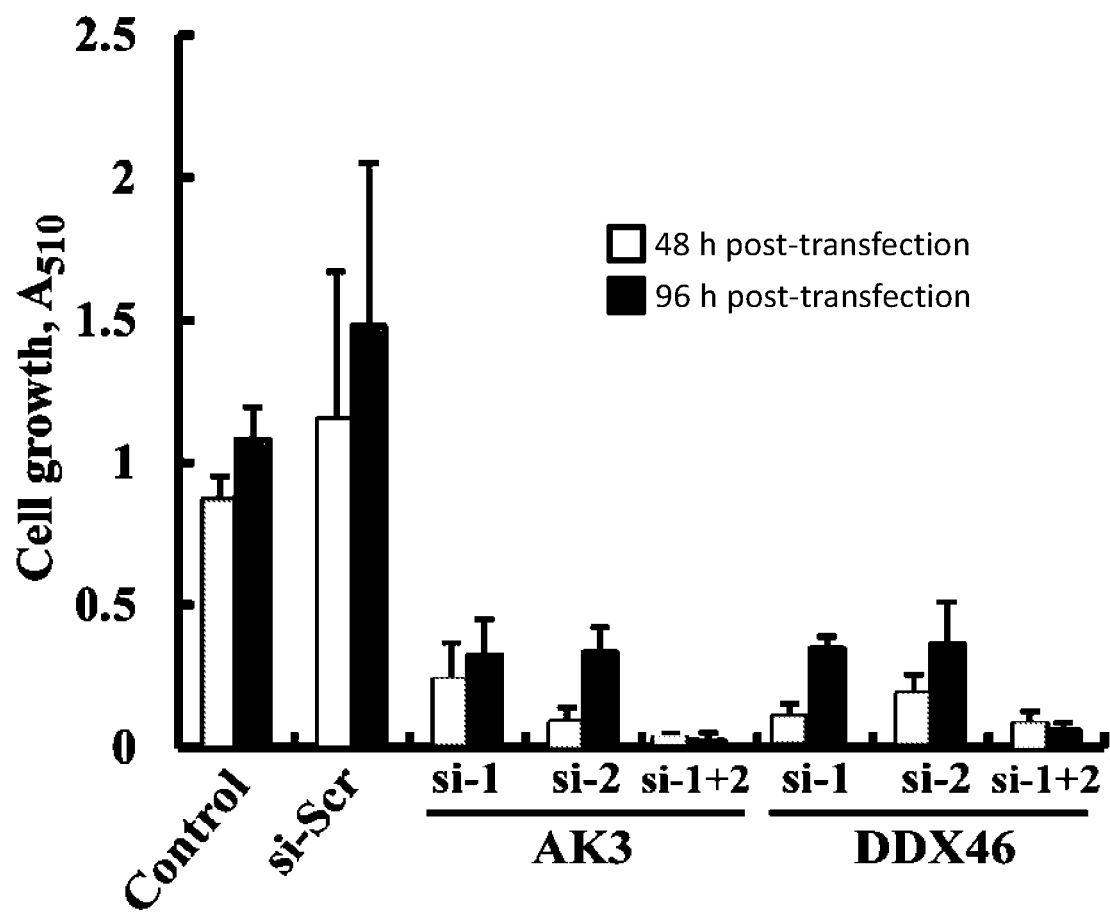
Figure 9A:
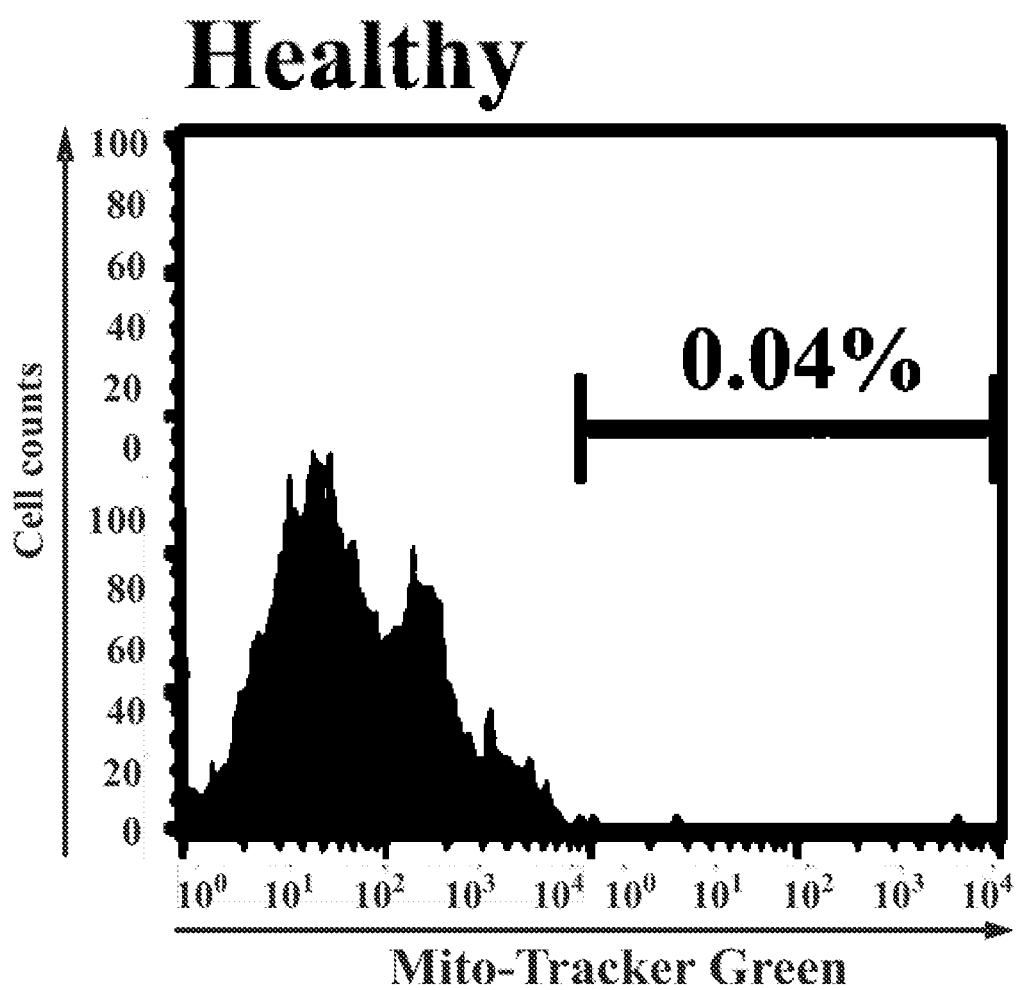
FIGS. 9A-9D show similar levels of mitochondria in PBMCs derived from CLL patients and healthy donors. The amounts of mitochondria in PBMCs derived from CLL patients and healthy donors were analyzed using MitoTracker green (unstained (A, B), stained (C, D)). Results are representative of three similar experiments.
Figure 9B:
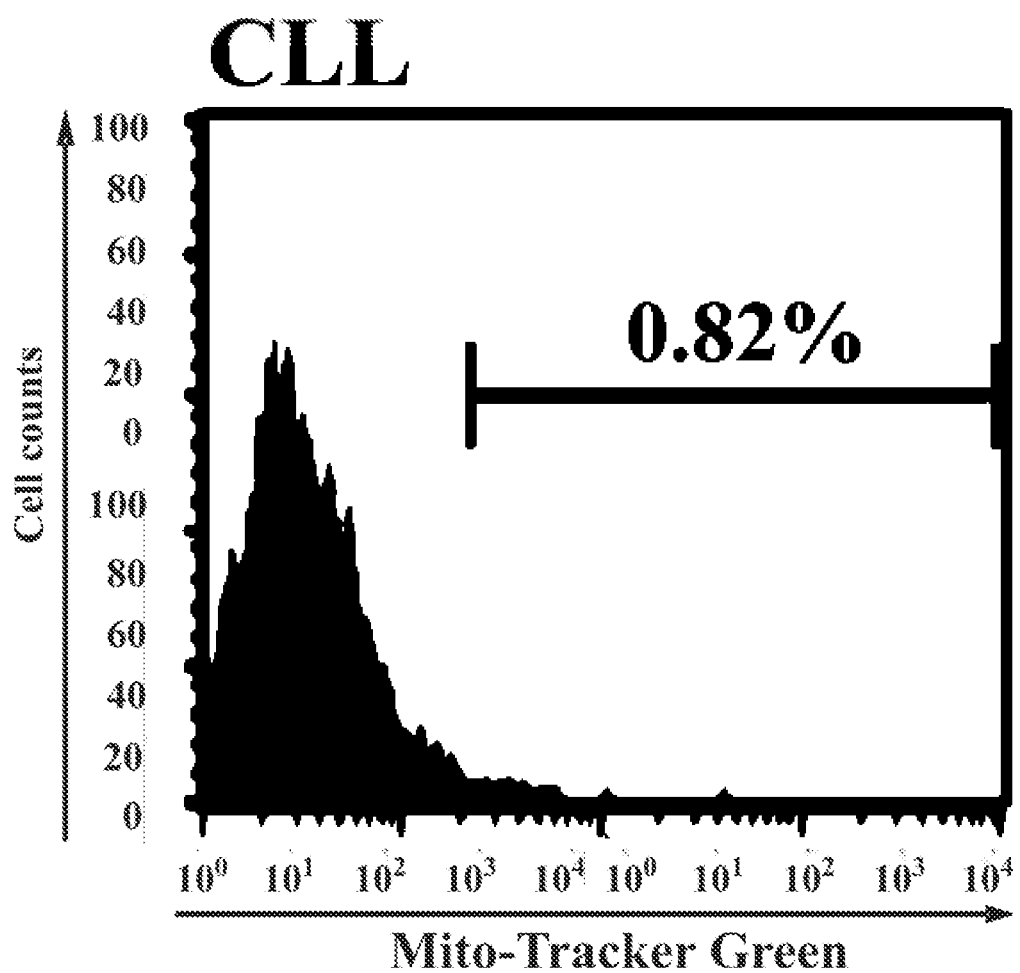
Figure 9C:
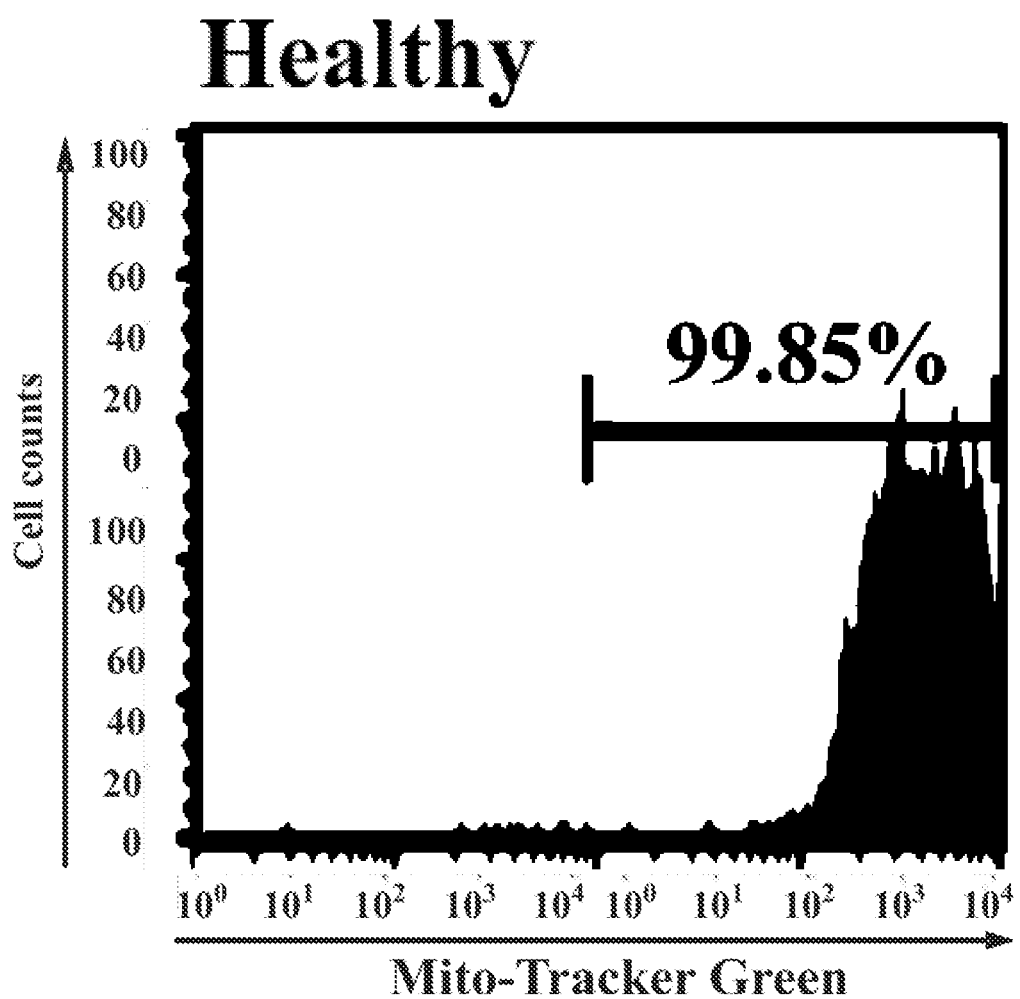
Figure 9D:
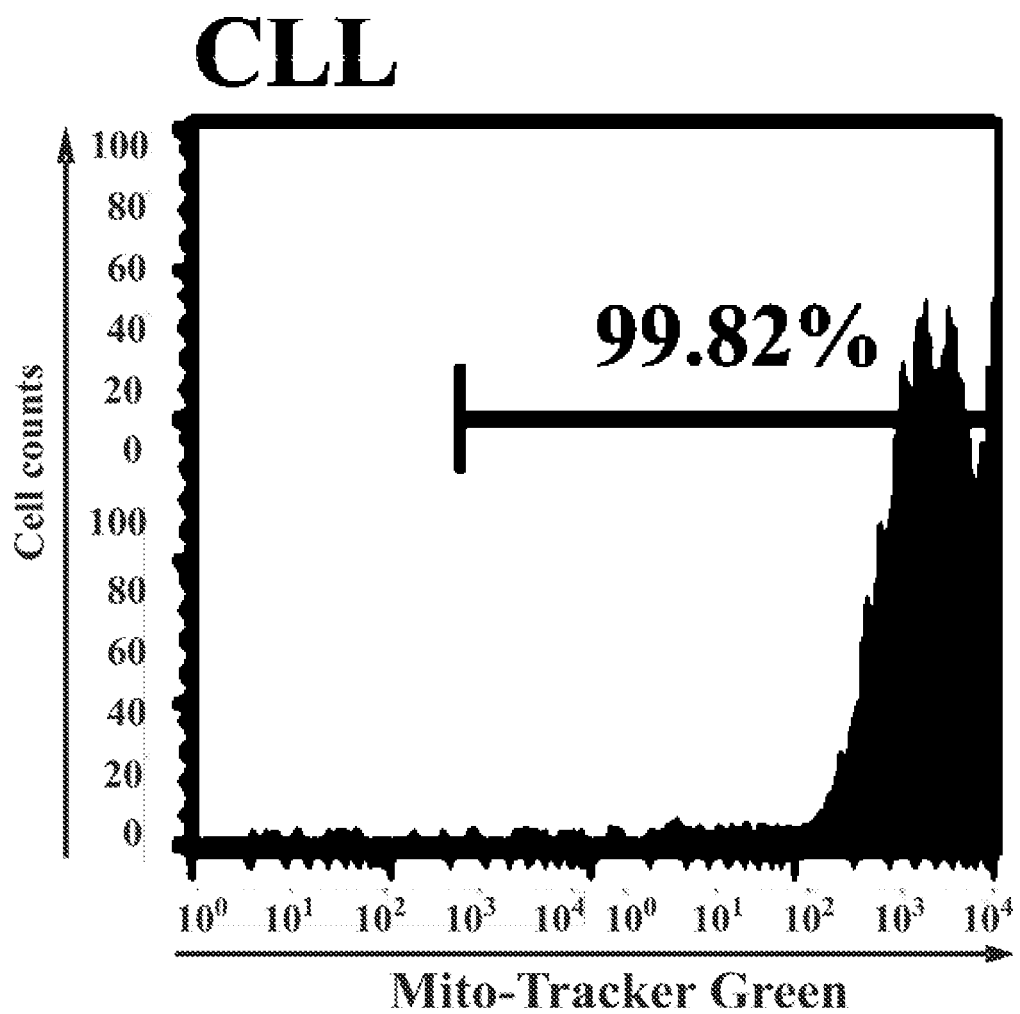

To verify the importance of these proteins to CLL cancer cells, the effects of their silencing on cell viability and growth using specific siRNA was performed. Owing to limited access to CLL samples and their low stability, MEC-1 cells derived from B-chronic lymphocytic leukemia in prolymphocytoid transformation (Stacchini A, et al., Leuk Res. 1999 February; 23(2):127-36) were used to analyze the effects of siRNA-mediated down-regulated expression of DDX46 and AK3 on cell viability (FIG. 8C). While two sets of siRNA were designed and tested for each of four proteins, only those designed for DDX46 and AK3 effectively decreased their expression (FIGS. 8A-8B). Cells were transfected with scrambled siRNA or siRNA specific to DDX46 or AK3 and cell growth was analyzed using the SRB method. Each of the designed siRNAs was highly effective in decreasing cell growth up to 80% 48 h post-transfection, with the combination of both siRNAs being more active in decreasing both mRNA levels and cell growth (over 90%) (FIGS. 8A-8C). These effects required only nanomolar concentrations (50 nM) and persisted 96 h post-transfection (FIGS. 8A-8C). The decrease in cell growth was due to a decrease in the number of cells and not due to cell death (data not shown).

The observed increases in protein levels were not due to increased mitochondrial numbers/mass, since analysis using MitoTracker green, a dye that localizes to mitochondria regardless of mitochondrial membrane potential, revealed similar levels of mitochondria in PBMCs derived from either CLL patients or healthy donors (FIGS. 9A-9D).

Overall, the results offer novel biomarkers for CLL diagnosis and prognosis, and provide treatment guidance.

Example 5: Clinical Characterization of the CLL Patients that Participated in the Study All patients were untreated at the time of this study. Patients' average age was 69 years, composed 14 males and 17 females. The T cell specific zeta-associated protein 70 (Zap 70) is an intracellular tyrosine kinase. ZAP-70 is the gene used to distinguish the CLL subtypes. The expression of ZAP-70 and the co-expression of the T-cell antigen CD5 and B-cell surface antigens CD19 were analyzed in peripheral-blood samples from the patients with CLL using specific antibodies and flow cytometry. Positive (over 15%) and negative (less than 14%) signals are indicated by + and −, and ND indicates not determined. About 13% of the tested samples were ZAP-positive (Table 3).

TABLE 3

Clinical characteristics of patients with B-CLL.

| Name | Age, years | Rai stage of disease | WBC $10^3/\mu l$ | Zap 70 | CD5/CD19 % | Gender |
|---|---|---|---|---|---|---|
| CLL1 | 40 | 0 | 12 | ND | ND | M |
| CLL2 | 73 | IV | 133 | ND | ND | M |
| CLL3 | 72 | 0-I | 39 | − | ND | F |
| CLL5 | 78 | 0 | 12.2 | + | ND | F |
| CLL6 | 83 | I | 16.7 | ND | ND | F |
| CLL7 | 58 | IV | 57.6 | + | ND | F |
| CLL8 | 64 | II | 40 | + | ND | F |
| CLL9 | 56 | III | 56.8 | − | ND | M |
| CLL10 | 62 | I | 15.9 | − | ND | F |
| CLL11 | 62 | 0 | 28.8 | + | 75.7 | F |
| CLL13 | 57 | I | 18.8 | − | ND | M |
| CLL14 | 83 | I | 20 | ND | 60.7 | M |
| CLL15 | 82 | I | 29 | − | 58.3 | F |
| CLL16 | 75 | I | 27 | ND | 74 | M |
| CLL17 | 70 | III | 43 | − | 64.8 | F |
| CLL18 | 64 | 0-I | 20 | − | 64.6 | M |
| CLL19 | 56 | I | 36 | − | 13.4 | F |
| CLL21 | 56 | I | 40 | − | 77.2 | M |
| CLL23 | 52 | III | 147 | − | 78 | F |
| CLL25 | 84 | I | 67 | − | 83 | M |
| CLL27 | 80 | 0 | 33.4 | ND | 62 | F |
| CLL29 | 73 | I | 17 | ND | 60.6 | M |
| CLL30 | 80 | II | 71 | ND | 50.5 | F |
| CLL31 | 61 | 0 | 7 | − | 38.1 | M |
| CLL32 | 75 | I | 31 | − | 67 | F |
| CLL41 | 75 | 0 | 15 | − | ND | F |
| CLL42 | 85 | I | 26 | ND | 81 | M |
| CLL46 | 83 | I | 29.8 | ND | 55 | F |
| CLL47 | 78 | IV | 26.6 | ND | 65 | F |
| CLL50 | 61 | IV | 40 | ND | ND | M |
| CLL51 | 63 | IV | 64 | − | ND | M |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating a patient having chronic lymphocytic leukemia (CLL), comprising:
 (a) predicting or assessing the level of severity of the CLL by the steps of:
  (i) comparing the expression level of at least one protein or mRNA biomarker in a biological sample obtained from the patient to a reference value or a control sample, wherein the at least one biomarker is selected from the group consisting of: SNX18, DHRS4, TBL2, RPE, ENPP4, and any combination thereof;
  (ii) determining the level of severity of cancer, wherein an increase in the level of at least one biomarker selected from the group consisting of: SNX18, DHRS4, TBL2, RPE and any combination thereof and/or a decrease in the level of ENPP4 characterizes said patient as being expected to develop a severe form of the CLL; and
 (b) administering to said patient characterized as being expected to develop a severe form of the CLL a therapeutically effective amount of at least one agent that reduces the expression or activity of at least one protein selected from the group consisting of SNX18, DHRS4, TBL2, RPE and any combination thereof, wherein the agent is an RNA interfering molecule.

2. The method of claim 1, wherein the reference value or control sample is obtained from a subject having a stable state of chronic lymphocytic leukemia.

3. The method of claim 1, wherein the reference value is an average value determined in a plurality of samples obtained from subjects having a stable state of chronic lymphocytic leukemia.

4. The method of claim 1, wherein the control sample is obtained from a healthy subject.

5. The method of claim 1, wherein assessing the level of severity comprises comparing the level of at least two biomarkers.

6. The method of claim 5, wherein the two biomarkers are SNX18 and RPE.

7. The method of claim 1, wherein the method comprises comparing the level of at least three biomarkers.

8. The method of claim 1, wherein the biological sample is whole blood or a fraction thereof.

9. The method of claim 1, wherein the increase of expression level is by a ratio of at least 2-fold relative to the control sample.

10. The method of claim 1, wherein the interfering RNA molecule is selected from the group consisting of: a shRNA, a siRNA, and a miRNA.

* * * * *

SEQUENCE LISTING

```
<160> NUMBER OF SEQ ID NOS: 16

<210> SEQ ID NO 1
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 1
aaguugaucu ucagacagcc cuu                                           23

<210> SEQ ID NO 2
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic
```

```
<400> SEQUENCE: 2
aagggcuguc ugaagaucaa cuu                                          23

<210> SEQ ID NO 3
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 3
aauccugggu ccagugugga auu                                          23

<210> SEQ ID NO 4
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 4
aauuccacac uggacccagg auu                                          23

<210> SEQ ID NO 5
<211> LENGTH: 25
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 5
cagagacggu uaucaagaga cuaaa                                        25

<210> SEQ ID NO 6
<211> LENGTH: 25
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 6
uuuagucucu ugauaaccgu cucug                                        25

<210> SEQ ID NO 7
<211> LENGTH: 25
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 7
ccaacaagau uuggcccuau guaua                                        25
```

```
<210> SEQ ID NO 8
<211> LENGTH: 25
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 8
uauacauagg gccaaaucuu guugg                                            25

<210> SEQ ID NO 9
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 9
gcaaacaucc cagaggguau                                                  19

<210> SEQ ID NO 10
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 10
auaccucugg gauguuugc                                                   19

<210> SEQ ID NO 11
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 11
gccccaaacc aattaaatcc tg                                               22

<210> SEQ ID NO 12
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 12
caatgccaat caaatctcgt cc                                               22

<210> SEQ ID NO 13
<211> LENGTH: 21
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 13
ttactgctcg ctggattcat c                                              21

<210> SEQ ID NO 14
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 14
gtctcttgat aaccgtctct gg                                             22

<210> SEQ ID NO 15
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 15
actcttccag ccttccttcc                                                20

<210> SEQ ID NO 16
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 16
tgttggcgta caggtctttg                                                20
```